US012369986B2

(12) United States Patent
DiMaio et al.

(10) Patent No.: US 12,369,986 B2
(45) Date of Patent: Jul. 29, 2025

(54) METHODS OF GUIDING MANUAL MOVEMENT OF MEDICAL SYSTEMS

(71) Applicant: INTUITIVE SURGICAL OPERATIONS INC., Sunnyvale, CA (US)

(72) Inventors: Simon Peter DiMaio, San Carlos, CA (US); Brandon Itkowitz, San Jose, CA (US); Govinda Payyavula, Fremont, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 1354 days.

(21) Appl. No.: 16/967,525

(22) PCT Filed: Feb. 4, 2019

(86) PCT No.: PCT/US2019/016549
§ 371 (c)(1),
(2) Date: Aug. 5, 2020

(87) PCT Pub. No.: WO2019/177711
PCT Pub. Date: Sep. 19, 2019

(65) Prior Publication Data
US 2021/0228282 A1 Jul. 29, 2021

Related U.S. Application Data

(60) Provisional application No. 62/642,299, filed on Mar. 13, 2018.

(51) Int. Cl.
*G06T 19/00* (2011.01)
*A61B 34/00* (2016.01)
(Continued)

(52) U.S. Cl.
CPC .............. *A61B 34/20* (2016.02); *A61B 34/70* (2016.02); *A61B 90/37* (2016.02); *G06T 19/006* (2013.01);
(Continued)

(58) Field of Classification Search
CPC ....... G06T 19/006; A61B 34/20; A61B 34/70; G16H 20/40
(Continued)

(56) References Cited

U.S. PATENT DOCUMENTS 6,120,433 A * 9/2000 Mizuno ................. A61B 34/76
600/102
7,239,330 B2 7/2007 Sauer et al.
(Continued)

FOREIGN PATENT DOCUMENTS

CN 106687046 A 5/2017
EP 2996615 A1 3/2016
(Continued)

OTHER PUBLICATIONS

US 9,980,782 B1, 05/2018, Gibby (withdrawn)
(Continued)

*Primary Examiner* — Thomas J Lett
(74) *Attorney, Agent, or Firm* — MARSHALL, GERSTEIN & BORUN LLP

(57) ABSTRACT

A computer-assisted medical system includes a user device wearable by an operator. The user device includes a display device configured to present imagery overlaid in an environment of a manipulator assembly, and a sensor configured to detect one or more landmarks in the environment. The medical system includes a controller configured to execute instructions to perform operations The operations include receiving, from the sensor, position or orientation information for the one or more landmarks in the environment, and
(Continued)

directing a manual movement of a portion of the manipulator assembly by causing the display device to present the imagery overlaid in the environment based on the received position or orientation information.

26 Claims, 9 Drawing Sheets

(51) Int. Cl.
　　*A61B 34/20*　　　　(2016.01)
　　*A61B 90/00*　　　　(2016.01)
　　*G16H 20/40*　　　　(2018.01)
　　*G16H 30/40*　　　　(2018.01)
　　*G16H 40/63*　　　　(2018.01)
　　*A61B 17/00*　　　　(2006.01)
　　*A61B 90/50*　　　　(2016.01)

(52) U.S. Cl.
　　CPC ............. *G16H 20/40* (2018.01); *G16H 30/40* (2018.01); *G16H 40/63* (2018.01); *A61B 2017/00207* (2013.01); *A61B 2034/2048* (2016.02); *A61B 2090/365* (2016.02); *A61B 2090/502* (2016.02)

(58) Field of Classification Search
　　USPC ......................................................... 345/633
　　See application file for complete search history.

(56) References Cited

U.S. PATENT DOCUMENTS

| | | | |
|---|---|---|---|
| 7,774,044 | B2 | 8/2010 | Sauer et al. |
| 9,521,961 | B2* | 12/2016 | Silverstein ............. A61B 8/463 |
| 9,538,962 | B1 | 1/2017 | Hannaford et al. |
| 9,645,785 | B1 | 5/2017 | Hannaford et al. |
| 9,681,925 | B2 | 6/2017 | Azar et al. |
| 9,767,608 | B2 | 9/2017 | Lee et al. |
| 9,892,564 | B1 | 2/2018 | Cvetko et al. |
| 9,980,780 | B2 | 5/2018 | Lang |
| 10,010,379 | B1 | 7/2018 | Gibby et al. |
| 10,799,294 | B2* | 10/2020 | Rotenberg ............. A61B 34/10 |
| 2007/0236514 | A1 | 10/2007 | Agusanto et al. |
| 2014/0276855 | A1 | 9/2014 | De La Barrera et al. |
| 2015/0366628 | A1 | 12/2015 | Ingmanson |
| 2016/0191887 | A1 | 6/2016 | Casas |
| 2016/0287337 | A1 | 10/2016 | Aram et al. |
| 2017/0135775 | A1 | 5/2017 | Cunningham et al. |
| 2017/0172696 | A1 | 6/2017 | Saget et al. |
| 2017/0333137 | A1 | 11/2017 | Roessler |
| 2017/0360395 | A1 | 12/2017 | Razzaque et al. |
| 2018/0032130 | A1 | 2/2018 | Meglan |
| 2018/0116732 | A1 | 5/2018 | Lin et al. |
| 2018/0140362 | A1 | 5/2018 | Caliet al. |
| 2018/0225993 | A1* | 8/2018 | Buras ..................... G09B 5/065 |
| 2019/0378276 | A1* | 12/2019 | Flossmann ................ G06T 7/60 |
| 2020/0038120 | A1* | 2/2020 | Ziraknejad .......... G06F 3/04815 |
| 2020/0060914 | A1* | 2/2020 | Lim ....................... A61B 34/30 |
| 2020/0243193 | A1* | 7/2020 | Plahey ................... G16H 40/63 |
| 2021/0038340 | A1 | 2/2021 | Itkowitz et al. |
| 2021/0128262 | A1 | 5/2021 | Gomez et al. |

FOREIGN PATENT DOCUMENTS

| | | |
|---|---|---|
| EP | 3157435 A1 | 4/2017 |
| EP | 3482710 A1 | 5/2019 |
| KR | 20140112207 A | 9/2014 |
| KR | 101471852 B1 | 12/2014 |
| WO | WO-2010039394 A1 | 4/2010 |
| WO | WO-2014151550 A2 | 9/2014 |
| WO | WO-2016014385 A2 | 1/2016 |
| WO | WO-2016149345 A1 | 9/2016 |
| WO | WO-2016162789 A3 | 11/2016 |
| WO | WO-2016207628 A1 | 12/2016 |
| WO | WO-2017151752 A1 | 9/2017 |
| WO | WO-2017151999 A1 | 9/2017 |
| WO | WO-2018022523 A1 | 2/2018 |
| WO | WO-2018032083 A1 | 2/2018 |
| WO | WO-2018052795 A1 | 3/2018 |
| WO | WO-2018052796 A1 | 3/2018 |
| WO | WO-2018052966 A1 | 3/2018 |
| WO | WO-2018118411 A1 | 6/2018 |

OTHER PUBLICATIONS

Bornik A., et al., "Computer Aided Liver Surgery Planning: An Augmented Reality Approach," Proceedings SPIE, May 30, 2003, vol. 5029, 12 pages.

Bornik A., et al., "Computer Aided Liver Surgery Planning Based on Augmented Reality Techniques," Image Processing for Medicine, 2003, Retrieved from the Internet: URL: http://ftp.informatik.rwth-aachen.de/Publications/CEUR-WS/Vol-80/p249.pdf, pp. 249-253.

International Search Report and Written Opinion for Application No. PCT/US2019/016549, mailed on May 21, 2019, 19 pages (ISRG11770/PCT).

Kalkofen D., et al., "Integrated Surgical Workflow for Augmented Reality Applications," AMI-ARCS 2006, Retrieved from the Internet: URL: http://campar.in.tum.de/files/amiarcs06/Kalkofen_-_Medica_Workflow.pdf, 8 pages.

Kogkas A.A., et al., "Gaze-contingent Perceptually Enabled Interactions in the Operating Theatre," International Journal of Computer Assisted Radiology and Surgery, Jul. 2017, vol. 12 (7), pp. 1131-1140.

Novak-Marcincin J., et al., "Augmented Reality Aided Manufacturing," Procedia Computer Science, 2013, vol. 25, pp. 23-31.

Splechtna R.C., et al., "ARAS—Augmented Reality Aided Surgery System Description," VRVis Research Center, 2002, Retrieved from the Internet: URL: http://citeseerx.ist.psu.edu/viewdoc/download?doi=10.1.1.12.5225&rep=rep1&type=pdf, 10 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wen R., et al., "Augmented Reality Guidance with Multimodality Imaging Data and Depth-Perceived Interaction for Robot-Assisted Surgery," Robotics, 2017, vol. 6 (2), 18 pages.

Extended European Search Report for Application No. EP19767575.4 mailed on Apr. 23, 2021, 09 pages.

* cited by examiner

METHODS OF GUIDING MANUAL MOVEMENT OF MEDICAL SYSTEMS

CROSS-REFERENCE TO RELATED APPLICATIONS

This application is a U.S. National Stage Application under 35 U.S.C. § 371 and claims the benefit of International Application Serial No. PCT/US2019/016549, filed on Feb. 4, 2019, which claims priority to U.S. Provisional Application Ser. No. 62/642,299, filed on Mar. 13, 2018, the entire contents of both of which are hereby incorporated by reference.

TECHNICAL FIELD

This specification relates to methods of guiding manual movement of medical systems.

BACKGROUND

A system of robotic devices can be used to perform a task at a worksite. For example, robotic systems can include robotic manipulators to manipulate instruments for performing the task. The robotic manipulator can include two or more links coupled together by one or more joints. The joints can be active joints that are actively controlled. The joints can also be passive joints that comply with movement of the active joints as the active joints are actively controlled. Such active and passive joints may be revolute or prismatic joints. The configuration of the robotic manipulator may then be determined by the positions and orientations of the joints, the structure of the robotic manipulator, and the coupling of the links.

Robotic systems include industrial and recreational robotic systems. Robotic systems also include medical robotic systems used in procedures for diagnosis, non-surgical treatment, surgical treatment, etc. As a specific example, robotic systems include minimally invasive, robotic telesurgical systems in which a surgeon can operate on a patient from bedside or a remote location. Telesurgery refers generally to surgery performed using surgical systems where the surgeon uses some form of remote control, e.g., a servomechanism, to manipulate surgical instrument movements rather than directly holding and moving the instruments by hand. A robotic medical system usable for telesurgery or other telemedical procedures can include a remotely controllable robotic manipulator. Operators can remotely control motion of the remotely controllable robotic manipulator. Operators can also manually move pieces of the robotic medical system into positions or orientations within its environment.

SUMMARY

In one aspect, a computer-assisted medical system includes a user device wearable by an operator. The user device includes a display device configured to present imagery overlaid in an environment of a manipulator assembly, and a sensor configured to detect one or more landmarks in the environment. The medical system includes a controller configured to execute instructions to perform operations. The operations include receiving, from the sensor, position or orientation information for the one or more landmarks in the environment, and directing a manual movement of a portion of the manipulator assembly by causing the display device to present the imagery overlaid in the environment based on the received position or orientation information.

In another aspect, a method of setting up a computer-assisted medical system including a manipulator assembly is featured. The method includes receiving, from a sensor of a user device of the computer-assisted medical system, position or orientation information for one or more landmarks in an environment. The method further includes directing a manual movement of a portion of the manipulator assembly by causing a display device of the user device to present imagery overlaid in the environment based on the received position or orientation information.

Advantages of the foregoing may include, but are not limited to, those described below and herein elsewhere. The systems and methods described herein can improve accuracy and precision of manual movement of an object in an environment. An operator wearing a user device can easily see a recommended position, orientation, and configuration for the object relative to an actual position, orientation, and configuration for the object, as the imagery is directly overlaid on the environment.

The systems and methods described herein can also improve workflow efficiency and safety. The user device can present imagery to guide tasks to be performed by the operator without drawing the operator's attention away from the environment. The operator can view and interact with the environment while simultaneously viewing guidance provided by the imagery presented by the user device. In implementations in which multiple user devices for multiple operators are present, the operators can easily collaborate with one another to prepare an environment and objects in the environment for a procedure to perform on a workpiece. For example, the operators can interact with the user devices to collaboratively update information presented on the user devices so that information is efficiently propagated to each of the operators. In addition, the operators can track the progress of tasks that other operators are performing, which can thereby make workflow more efficient.

The details of one or more implementations of the subject matter described in this specification are set forth in the accompanying drawings and the description below. Other potential features, aspects, and advantages will become apparent from the description, the drawings, and the claims.

DETAILED DESCRIPTION

Figure 1A:
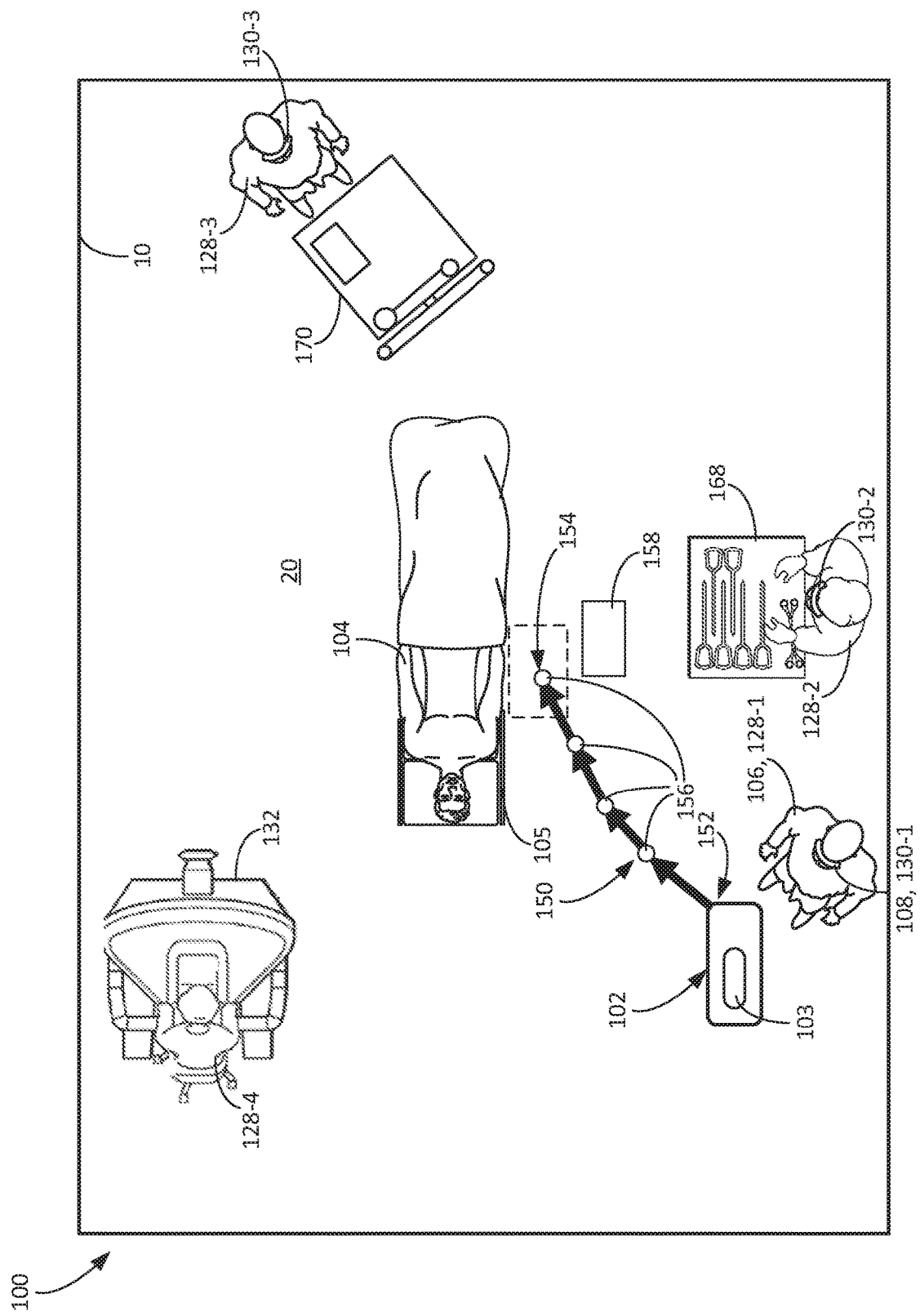
FIG. 1A is a top view of a medical environment including a robotic device with a depiction of imagery in the environment presented to an operator through a user device.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that includes, or does not include, surgical aspects.
Example Systems Starting with a medical example shown in FIG. 1A, a computer-assisted medical system 100 in an environment 10 includes a robotic manipulator assembly 102 with a robotic manipulator 103. The medical system 100 can be operated to perform a procedure on a workpiece, e.g., to perform a medical procedure on a patient 104. One or more operators (e.g., one or more of surgeons, surgical assistants, nurses, technicians, and other medical practitioners) can operate the medical system 100 or portions of the medical system 100 to perform the surgery.

A configuration of the manipulator assembly 102 can be established in preparation for performing the medical procedure on the patient 104. The manipulator assembly 102 or portions of the manipulator assembly 102 can be manually moved, e.g., repositioned or reoriented, relative to the patient 104 such that the manipulator 103 of the manipulator assembly 102 can be used to perform the medical procedure on the patient 104. In some examples, the manipulator assembly 102 has a recommended configuration, e.g., recommended by a controller of the medical system 100 based on data such as presets, input data from sensors or users, etc. An operator 106 manually moves the manipulator assembly 102 into the recommended configuration. The recommended configuration of the manipulator assembly 102 can be defined by positions and orientations of individual components of the manipulator assembly 102. In some examples, the manipulator assembly 102 may be manually translated in its entirety across a floor surface 20 to reposition the manipulator 103 relative to the patient 104. In further examples, the manipulator assembly 102 can be manually reoriented to reorient the manipulator 103 relative to the patient 104. In further examples, the manipulator 103 or a portion of the manipulator 103 is translated or reoriented in the environment 10. As described herein, a user device 108 of the operator 106 can direct the manual movement of the manipulator assembly 102, the manipulator 103, a portion of the manipulator assembly 102, or a portion of the manipulator 103 by presenting imagery overlaid in the environment 10.

To control the user device 108, a controller 122 (shown in FIG. 4) receives information pertaining to one or more landmarks in the environment 10 to localize the user device 108 worn by the operator 106, e.g., using simultaneous localization and mapping (SLAM) techniques. A landmark can correspond to any physical object in the environment 10, such as an operating table 105, the patient 104, another manipulator in the environment 10, other equipment in the environment 10, a feature on a wall surface in the environment 10, a feature on a floor surface in the environment 10, or other unique features that can be used (as described herein) to localize the user device 108 in the environment 10. The controller 122 then controls the user device 108 to present imagery to the operator 106 equipped with the user device 108. The imagery can be presented in manner such that the imagery appears, to the operator 106 equipped with the user device 108, overlaid in the environment 10 based on the received information. This overlaid information is used to direct manual movement facilitated by the operator 106 to move the manipulator 103 or a portion of the manipulator 103 to a recommended position or orientation.

Figure 1B:
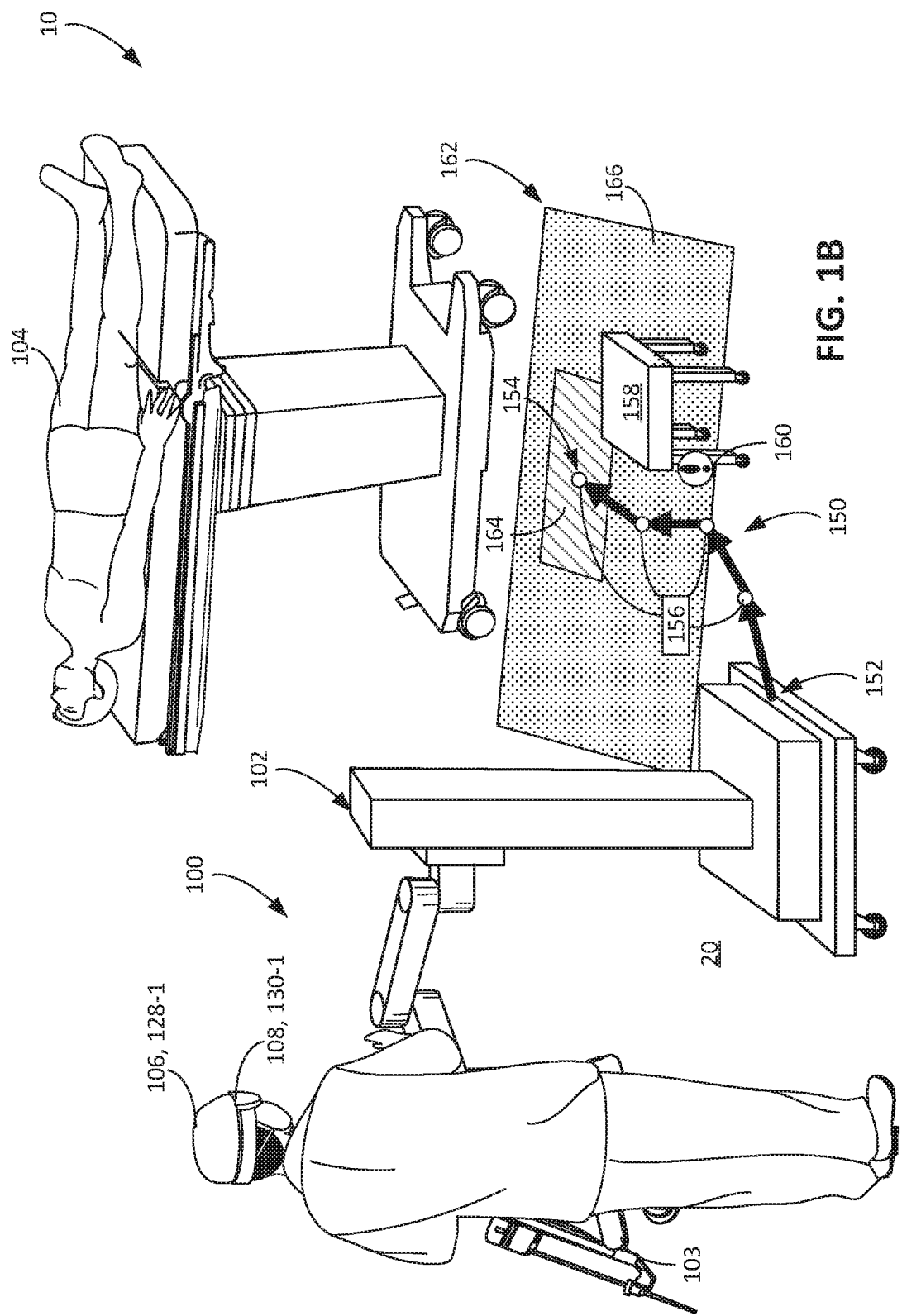
FIG. 1B is a perspective view of an isolated portion of the environment of FIG. 1A.

FIGS. 1A and 1B depict an example of imagery overlaid in the environment 10. The controller 122 causes a display device 124 (shown in FIG. 3) of the user device 108 to present imagery overlaid with a floor surface 20 in the environment 10.

The display device 124 presents imagery that indicates a path 150 along the floor surface 20. For example, the imagery includes a representation of the path 150 that appears, to the operator 106 wearing the user device 108, to be overlaid with the environment 10, the floor surface 20, or other portions of the environment 10. The path 150 is indicative of a recommended path along which the manipulator assembly 102 should be manually moved to arrive at its recommended location. The recommended location and the recommended path can be determined based on various forms of input data, e.g., including input data 600 described with respect to FIG. 6. In some examples, when the manipulator assembly 102 is at the recommended location, the manipulator 103 can easily access the patient 104. In cases in which the imagery is used to guide repositioning of the manipulator assembly 102 in its entirety, the path 150 is indicative of a current location 152 of the manipulator assembly 102 and a recommended location 154 of the manipulator assembly 102. The path 150 guides repositioning from the current location 152 of the manipulator assembly 102 toward the recommended location 154 of the manipulator assembly 102. The operator 106 manually moves the manipulator assembly 102 in its entirety along the path 150 from the current location 152 to the recommended location 154.

In some implementations, in addition to being indicative of the current location 152 and the recommended location 154, the path 150 is indicative of multiple waypoints 156 along the floor surface 20. These recommended waypoints 156 for the manipulator assembly 102 are selected such that the manipulator assembly 102 is kept away from contacting other objects in the environment 10 when the manipulator assembly 102 is manually moved along the path 150. In one example, an obstacle, e.g., a chair 158, is located in the environment 10 between the manipulator assembly 102 and the patient 104. The waypoints 156 are selected so that the manipulator assembly 102 is maneuvered away from the chair 158. In some implementations, the imagery presented by the user device 108 includes an indicator 160 that the chair 158 is proximate to the path 150. This indicator 160 notifies the operator 106 of potential obstacles with which the manipulator assembly 102 could collide when moved along the path 150. FIG. 1B depicts four waypoints 156, but fewer or more waypoints can be present in other implementations.

As shown in FIG. 1B, the imagery includes a map 162 indicative of desirable locations and undesirable locations for the manipulator assembly 102. The map 162 can be overlaid on the floor surface 20 and the environment 10 so that the operator 106 equipped with the user device 108 can easily see where the desirable locations for the manipulator assembly 102 are in the environment 10. A region 164 of the map 162 is indicative of the desirable locations, while a region 166 of the map 162 is indicative of the undesirable locations. The region 164 is positioned proximate the patient 104 and the operating table 105 and is selected by the controller 122 to include locations determined to be easily accessible by the manipulator assembly 102. The region 166 corresponds to locations that would be undesirable for the manipulator assembly 102. In some implementations, rather than indicating all undesirable locations of the manipulator assembly 102, the region 166 indicates locations that are near the patient 104 and the operating table 105 but that would be undesirable because, for example, the manipulator 103 would be too far from the patient 104 and the operating table 105 or would be near an obstacle with which the manipulator 103 could collide during a procedure.

In some implementations, to produce the imagery including the regions 164, 166, the controller 122 determines a desirability value of each potential location for the manipulator assembly 102. The controller 122 then designates locations having a desirability value above a predefined threshold as being desirable locations, e.g., corresponding to the locations in the region 164, and designates locations having a desirability value less than or equal to the predefined threshold as being undesirable locations, e.g., corresponding to the locations in the region 166. In some examples, rather than showing two discrete regions, the map 162 is a heat map that is indicative of a desirability value for each potential location. The map 162 can include a color-code representation of the desirability values. If the map 162 is a heat map, the map 162 can be indicative of more than two regions, each of the regions being indicative of a different predefined range of desirability values. The desirable locations, the undesirable locations, the waypoints 156, the indicator 160, the map 162, the region 164, and the region 166 can be generated based on various forms of input data, e.g., including the input data 600 described with respect to FIG. 6.

Figure 2:
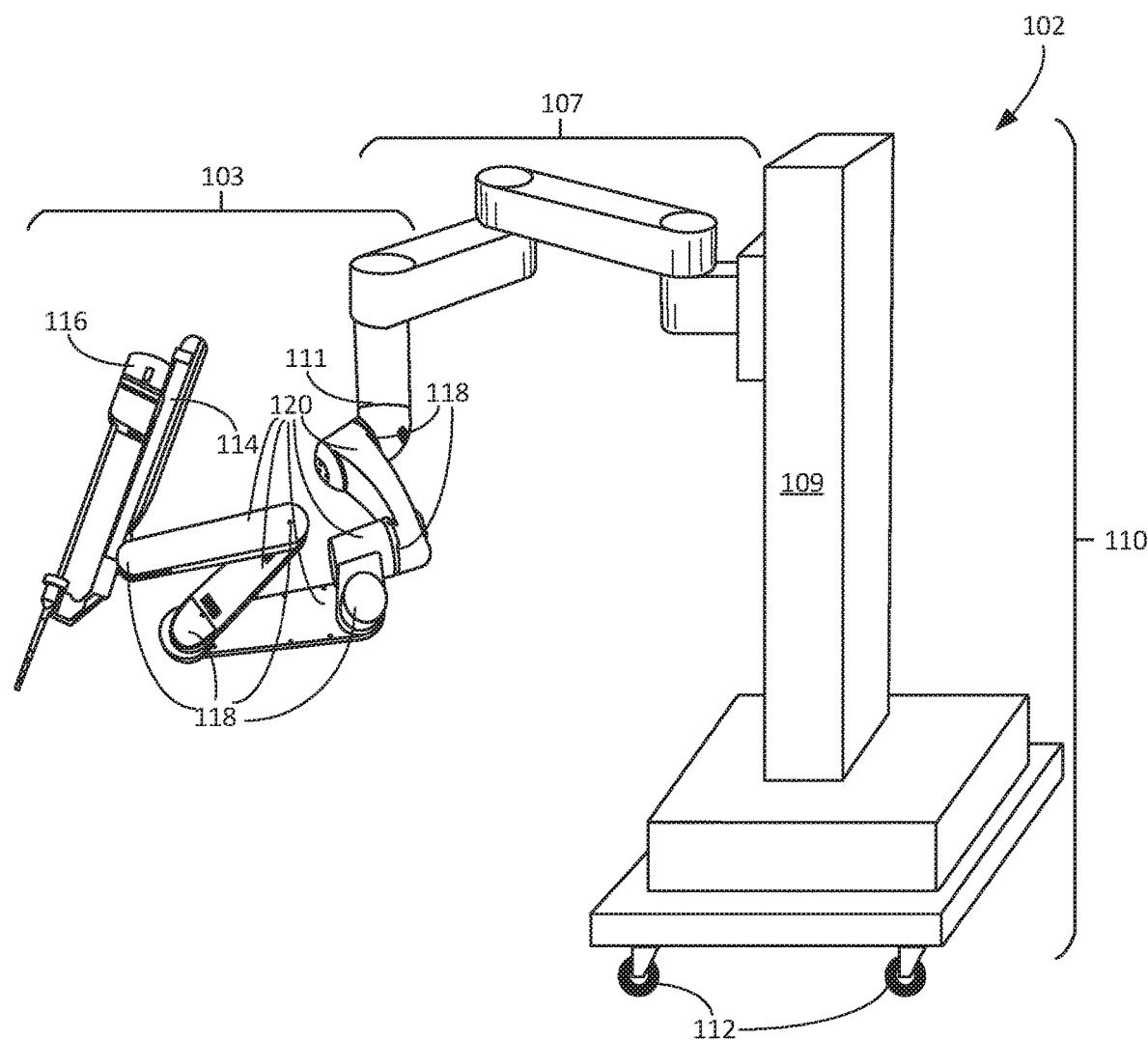
FIG. 2 is a perspective view of an example of a manipulator assembly.

FIG. 2 depicts an example of the manipulator assembly 102 that is movable across the floor surface 20 (shown in FIGS. 1A and 1B). In addition to including the manipulator 103, the manipulator assembly 102 includes a support structure 110 that supports the manipulator 103 above the floor surface 20. The support structure 110 is translatable and orientable relative to the floor surface 20. For example, the support structure 110 includes wheels 112, e.g., caster wheels, that enable the operator 106 (shown in FIGS. 1A and 1B) to manually reposition or reorient the support structure 110 relative to the patient 104 (shown in FIGS. 1A and 1B). The support structure 110 is connected to the manipulator 103 and supports the manipulator 103 at a height above the floor surface 20. In the example process of guiding manual movement of a portion of the manipulator assembly 102 described with respect to FIGS. 1A and 1B, the portion of the manipulator assembly 102 for which movement is guided can correspond to the support structure 110. In particular, the operator 106 can manually reposition the manipulator assembly 102 in its entirety by manually moving the support structure 110. In other examples, the portion can correspond to the manipulator 103, or another portion of the manipulator assembly 102.

The position or orientation of the manipulator 103 can be manually adjusted through other mechanisms. In one example, the height of the manipulator 103 above the floor surface 20 is adjustable. The manipulator 103 can be vertically movable relative to the support structure 110. In another example, the manipulator 103 can be reoriented relative to the support structure 110. The support structure 110 can include one or more passive joints about which the manipulator 103 can be rotated. In the example shown in FIG. 2, the support structure 110 can include a passive setup arm 107 connecting the manipulator 103 to a column 109 of the support structure 110. The passive setup arm 107 includes a series of passive links and joints that can be manually repositioned and reoriented. The passive setup arm 107 can be vertically translated relative to the column 109, thereby vertically repositioning the manipulator 103 relative to the column 109 of the support structure 110.

A base 111 of the manipulator 103 is connected to the support structure 110, e.g., to the passive setup arm 107 of the support structure 110. The manipulator 103 includes one or more joints and one or more links that are operable to move an instrument holder 114 that is configured to hold an instrument 116. The one or more links of the manipulator 103 extend distally from the base 111 of the manipulator 103. For example, the manipulator 103 includes joints 118 and links 120, and one or more of the joints 118 are powered joints that can be controlled by a controller 122 (shown in FIG. 4). In some implementations, one or more of the joints 118 are passive joints. By driving the joints 118, the instrument holder 114 with the instrument 116 can be repositioned relative to the patient 104 or the environment 10 (shown in FIG. 1). In preparation for a procedure, the base 111 of the manipulator 103 can be repositioned to a desirable location so that desired ranges of motion of the links 120 and the joints 118 of the manipulator 103 can be achieved. In this regard, in certain examples as described herein, the controller 122 (shown in FIG. 4) can cause the user device 108 (shown in FIG. 1) to present imagery to direct manual movement of the manipulator 103, a link 120, a joint 118, the base 111, or another portion of the manipulator 103.

Figure 3:
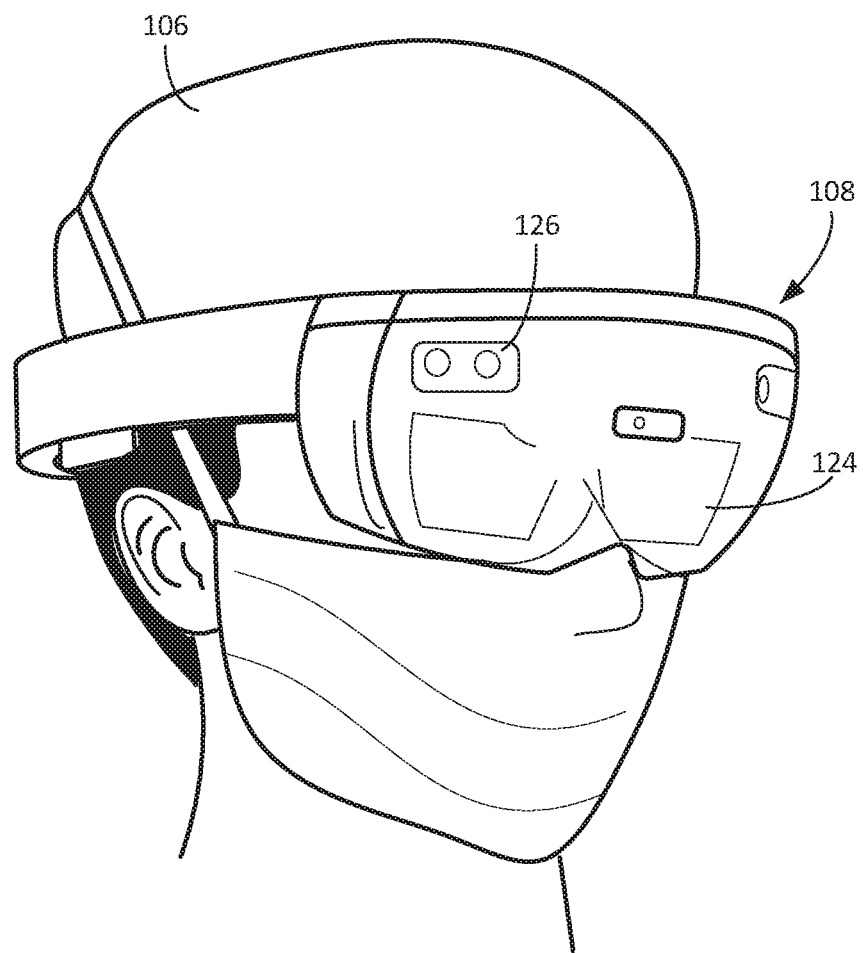
FIG. 3 is a front view of an operator wearing a user device.

FIG. 3 shows an example of the user device 108 worn by the operator 106. The user device 108 includes a display device 124 and a sensor 126. The display device 124 presents imagery to the operator 106. For example, in the example shown in FIG. 3, the user device 108 is a wearable head-mounted display device that can be worn over eyes of the operator 106. The display device 124 includes a see-through display that presents imagery. At least some of the imagery can be overlaid in the environment 10 when the user device 108 is worn over the eyes of the operator 106. At least some of the imagery can be transparent such that, when overlaid on a portion of the environment 10, this portion of the imagery and the portion of the environment 10 are both visible to the operator 106. In some implementations, at least some of the imagery overlaid on a portion of the environment 10 can be opaque such that the portion of the environment 10 is not visible to the operator 106 but this portion of the imagery is visible to the operator 106. A view frame of the display device 124 is in front of the eyes of the operator 106 so that imagery presented by the display device 124 appears overlaid on the portion of the environment 10 seen by the operator 106. The operator 106 thus simultaneously sees the environment 10 as well as any overlaid imagery that is presented on the display device 124.

The sensor 126 is configured to detect one or more landmarks in the environment 10 to generate information indicative of a position and/or orientation of one or more landmarks in the environment 10. The sensor 126 can generate one or more signals in response to detecting the one or more landmarks in the environment, and the one or more signals can be processed and analyzed, e.g., by the controller 122, to generate the information indicative of the position and/or orientation of the one or more landmarks. In some examples, the sensor 126 includes an image capture device that captures imagery of the environment 10, including any landmarks in the environment 10. The position and orientation information, using SLAM techniques, can be used to localize the user device 108 and hence the display device 124 relative to the environment 10 and other features within the environment 10 such that the imagery presented by the display device 124 can be overlaid in a manner that is meaningful to the operator 106 wearing the user device 108. In particular, from the perspective of the operator 106, the imagery appears to be overlaid on portions of the environment 10 so that the operator 106 can easily use the imagery as guidance for interacting with the environment 10.

Figure 4:
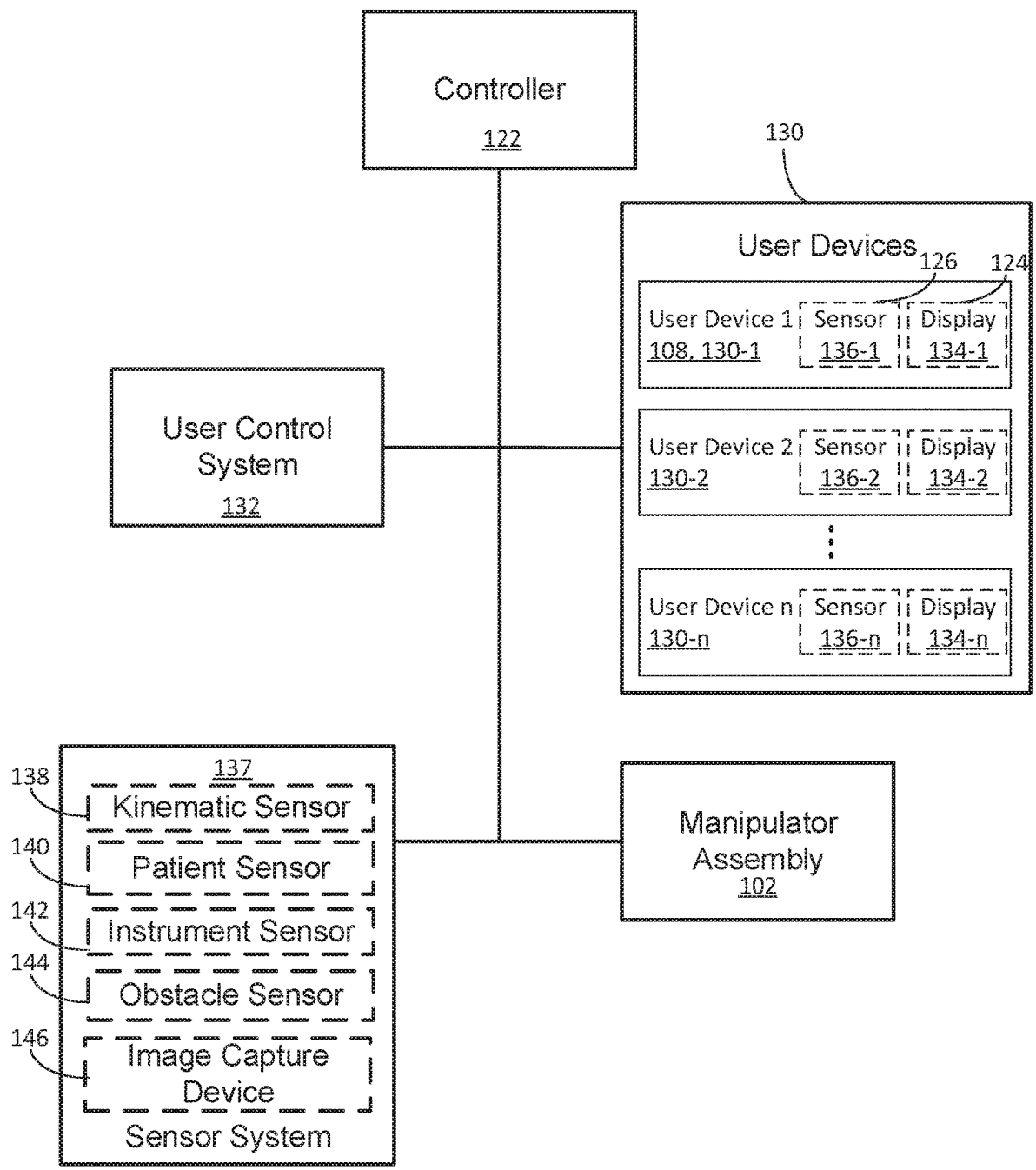
FIG. 4 is a block diagram of a robotic system.

FIG. 4 shows an example diagram of the medical system 100 that can be used for guiding the manual movement of the manipulator assembly 102. The medical system 100 includes the user device 108, manipulator assembly 102, and the controller 122. The controller 122 includes one or more computer processors. In some implementations, the controller 122 corresponds to a combination of processors of the manipulator assembly 102, the user device 108, and other systems of the medical system 100. The controller 122 directs operations of the various systems of the medical system 100.

In some implementations, the medical system 100 further includes a user control system 132 (also shown in FIG. 1A). The user control system 132 includes a user input system and a user output system. The user input system of the user control system 132 is operable by one of the operators 128 to control movement of the manipulator assembly 102. In some cases, a user device receives user commands from the operator 106 to move the teleoperated manipulator 103. In some cases, the user input system is manually operable such that manual operation of the user input system results in corresponding movement of the manipulator assembly 102. The user input system can include one or more of foot pedals with either or both of toe and heel controls, one or more joysticks, or other manually operable user input devices. In some cases, the user input system includes an image capture device or other sensor that can detect user motion. The user input system generates control signals to control movement of the manipulator assembly 102 based on the detected user motion. The user output system of the user control system 132 provides imagery of the worksite to the operator operating the user control system 132.

In cases in which the medical system 100 includes the user control system 132, the guidance of manual movement of the manipulator assembly 102 provided by the controller 122 can include guidance for operating the user input system of the user control system 132 to move the manipulator assembly 102. For example, if the user input system includes a user input device, the operator 106 manually operates the user input device to manually move the manipulator assembly 102. Alternatively, if the user input system includes an image capture device or another sensor that detects operator motion, the controller 122 operates the user device 108 to present imagery that guides the operator to move in a certain manner that causes the manipulator assembly 102 or a portion thereof to move.

The medical system 100 includes a sensor system 137, including the sensor 126 of the user device 108, that can detect features of the environment 10. The data produced by the sensor system 137 can be used with SLAM techniques to localize the user device 108 within the environment 10. With the data provided by the sensor system 137, a pose of the user device 108, e.g., a position and an orientation of the user device 108, relative to the environment 10 can be determined.

The sensor system 137 produces position or orientation information for one or more landmarks extracted from signals generated by the sensor system 137. A landmark is a unique signal or set of signals generated by the sensor system 137 that can be distinguished from other signals that could be generated by the sensor system 137 as the sensor system 137 detects different features within the environment 10. For example, in cases in which the sensor system 137 includes the sensor 126 of the user device 108 and the sensor 126 is an image capture device, a landmark can correspond to a unique visual feature in the environment 10 that generally does not change position or orientation relative to the environment 10, such as the operating table 105, other equipment in the environment 10, a corner of a room, or another unique visual feature. When such a visual feature is observed by the sensor 126, information received by the controller 122 from the sensor 126 is indicative of an orientation or a position of the landmark relative to the sensor 126, thus enabling the controller 122 to use SLAM techniques to determine a position or an orientation of the sensor 126 and hence the user device 108 relative to the environment 10.

The sensor system 137 can include one or more sensors in addition to the sensor 126 of the user device 108. For example, the medical system 100 includes one or more of a kinematic sensor 138, a patient sensor 140, an instrument sensor 142, an obstacle sensor 144, or an image capture device 146. Output data produced by the sensors of the sensor system 137 can be used by the controller 122 to localize the user device 108 in the environment 10. In some implementations, the output data can be used to provide other information to the operator 106 through the user device 108. In some examples described herein, the output data are used for determining a recommended configuration for the manipulator assembly 102 and hence for generating the imagery for guiding the manual movement of the manipulator assembly 102 toward the recommended configuration. In other examples, the output data are used to provide information related to a status of a certain subsystem of the medical system 100, a certain operator in the environment 10, the patient 104, or another object in the environment 10.

The kinematic sensor 138 can be a kinematic sensor of the manipulator assembly 102. For example, the kinematic sensor 138 can detect a pose of the joints 118 or the links 120 of the manipulator 103. In some cases, the kinematic sensor 138 is configured to detect a pose of the instrument holder 114 such that a position and orientation of the instrument 116 can be determined. The kinematic sensor 138 can be an accelerometer, a gyroscope, an encoder, a torque sensor, a force sensor, or other type of sensor that can detect motion of one of the joints 118 or the links 120 of the manipulator 103. In some examples, the manipulator assembly 102 includes a single kinematic sensor, whereas in other implementations, the manipulator assembly 102 includes two or more kinematic sensors.

The patient sensor 140 is configured to detect a characteristic of the patient 104 (shown in FIG. 1). For example, the patient sensor 140 can be a patient motion sensor that detects when the patient 104 moves, e.g., relative to the environment 10 or relative to an operating table 105 (shown in FIG. 1) on which the patient 104 is positioned. In some cases, the patient sensor 140 includes an image capture device or an optical sensor, e.g., mounted in the environment 10 or mounted to the manipulator 103, that detects whether the patient 104 is positioned on the operating table 105. In some cases, the patient sensor 140 includes an accelerometer or other motion sensor attached to the patient 104 that detect movement of the patient 104. In other cases, rather than detecting a motion or position of the patient 104, the patient sensor 140 detects another physical characteristic of the patient 104, such as a weight or a size of the patient 104, a blood pressure of the patient 104, a heart rate of the patient 104

The instrument sensor 142 is configured to detect a characteristic of the instrument 116 mounted to the instrument holder 114. The instrument sensor 142, for example, is a sensor on the instrument holder 114 that detects whether an instrument has been mounted to the instrument holder 114. In some implementations, the instrument sensor 142 detects a type of instrument 116 mounted to the instrument holder 114. For example, the instrument sensor 142 can be a sensor of the manipulator assembly 102 that detects an identity indicated in an EEPROM of the instrument 116. In some implementations, the instrument sensor 142 detects motion of the instrument 116. For example, the instrument sensor 142 includes an accelerometer, a gyroscope, a force sensor, a torque sensor, or other type of sensor mounted to the instrument 116 or the instrument holder 114 to detect motion of the instrument 116.

The obstacle sensor 144 is configured to detect obstacles in the environment 10. The obstacle sensor 144, in some cases, is an optical or acoustic proximity sensor that detects when obstacles are near the manipulator assembly 102. The obstacle sensor 144, for example, is mounted to the manipulator assembly 102 and is able to detect when an obstacle within a predetermined distance of the manipulator assembly 102. In some implementations, the obstacle sensor 144 is an image capture device mounted in the environment 10 and configured to detect when obstacles are moved win the vicinity of the manipulator assembly 102. The obstacles can include objects such as other equipment of the medical system 100, other equipment within the environment 10, persons in the environment 10, or other objects in the environment 10. The obstacle sensor 144 can include contact sensors, proximity sensors, optical time-of-flight sensors, and other sensors appropriate for detecting contact with an obstacle or a distance of an obstacle.

The image capture device 146 can correspond to one of the image capture devices described with respect to one of the other sensors described herein, e.g., one of the sensors 136 of the user devices 130, the kinematic sensor 138, the patient sensor 140, the instrument sensor 142, the obstacle sensor 144, or another sensor. The image capture device 146 is positioned within the environment 10 to capture imagery of the environment 10. In some cases, one of the user devices 130 includes the image capture device 146. In other cases, the image capture device 146 is fixed a part of the environment 10, e.g., a wall, a ceiling, or other fixture in the environment 10. The image capture device 146 can be an optical sensor, e.g., a camera, or an acoustic sensor.

Exemplary Processes

Figure 5A:
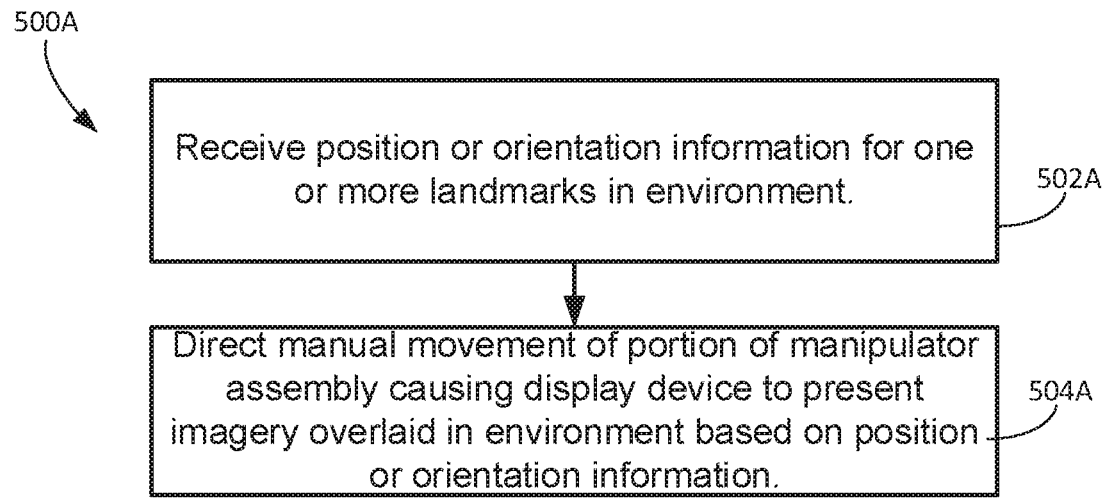
FIG. 5A is a flowchart of an example of a process of directing manual movement of a portion of a manipulator assembly.

FIG. 5A depicts a process 500A for guiding manual movement of a portion of the manipulator assembly 102 (shown in FIGS. 1A and 1B). As described herein, the portion of the manipulator assembly 102 can correspond to the support structure 110 of the manipulator assembly 102. The process 500A can be performed by the controller 122 described herein. At operation 502A, the controller 122 receives position or orientation information for one or more landmarks in an environment. For example, the controller 122 receives this information from one or more sensors, such as those described with respect to the sensor system 137 or with respect to the sensor 126 of the user device 108.

At operation 504A, the controller 122 directs manual movement of the portion of the manipulator assembly 102. The controller 122 causes the display device 124 of the user device 108 worn by the operator 106 (described with respect to FIGS. 1A, 1B, and 3) to present imagery overlaid in the environment 10 based on the position or orientation information received at the operation 502A. The imagery can be presented to guide the operator 106 to manually move the portion of manipulator assembly 102 toward a recommended configuration that is determined based on the position or orientation information received at the operation 502A. The imagery can also be presented such that the imagery is positioned or oriented relative to the environment 10 based on the position or orientation information received at the operation 502A. In some examples, the imagery indicates a recommended path of movement for the portion of the manipulator assembly 102, e.g., as described with respect to FIGS. 1A and 1B. As described herein, other examples are possible.

Figure 5B:
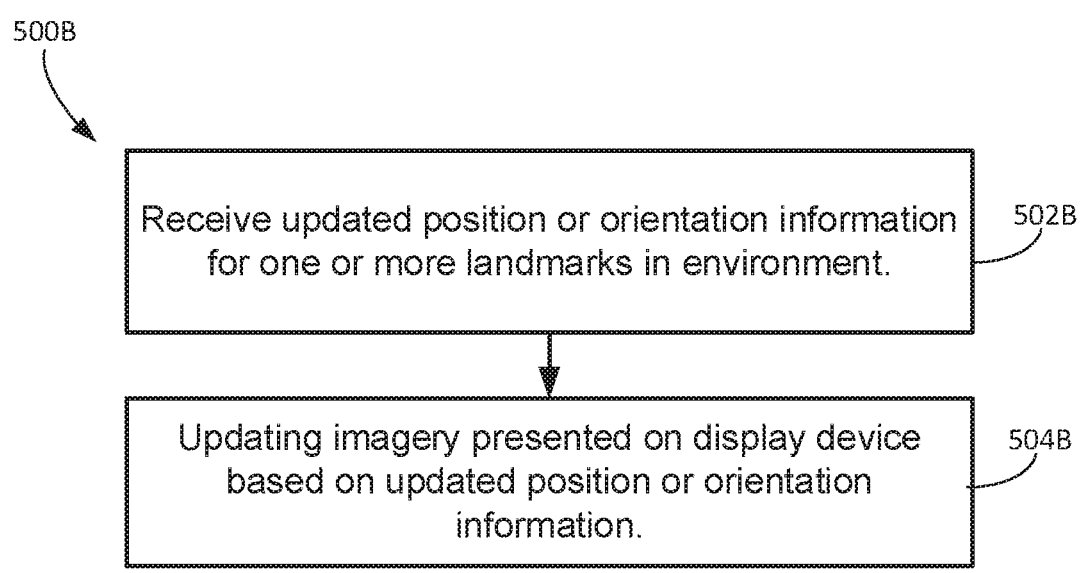
FIG. 5B is a flowchart of another example of a process of directing manual movement of a portion of a manipulator assembly.

FIG. 5B depicts another process 500B for updating imagery presented to the operator 106. In some cases, the process 500B is executed after the operation 502A of the process 500A is executed such that imagery has already been presented to the operator 106 through the user device 108 (shown in FIG. 1A). In the process 500B, at operation 502B, the controller 122 receives updated position or orientation information for the one or more landmarks in the environment, e.g., for the one or more landmarks in the environment for which information was received at the operation 502A. This updated position or orientation information can be indicative of movement of the operator 106, and hence the user device 108, relative to the one or more landmarks.

At operation 504B, the controller 122 updates the presented imagery based on the updated position or orientation information. For example, if the user device 108 has been moved relative to the one or more landmarks, the presented imagery can be updated such that the position or orientation of the imagery relative to the one or more landmarks is maintained even though the user device 108 has moved. In this regard, if a portion of the imagery is overlaid on an object in the environment, the presented imagery is updated so that the portion of the imagery remains overlaid on the object when the user device is moved relative to the object.

Alternative or Additional Implementations

A number of implementations have been described. Nevertheless, it will be understood that various modifications may be made to the processes, systems, and mechanisms described herein.

Some implementations described herein are described with respect to medical examples. In other implementations, the medical system 100 is a surgical system for performing a surgical procedure on the patient 104. The techniques disclosed herein are also applicable to non-surgical use. For example, they may be used with and improve general or industrial robotic operations, such as those use in manipulating work pieces. These techniques may also be used with and improve medical robotic operations for diagnoses and non-surgical treatment.

The specific examples presented in this disclosure can be applicable to teleoperational robotic systems and remotely controllable arms. The techniques disclosed herein are also applicable to robotic systems that are, in part or in whole, directly and manually moved by operators. For example, these techniques can be applied to robotic systems designed to help steady an instrument held by the manipulator 103 while the instrument is manipulated by hand of an operator. As another example, any of the controllable manipulators discussed herein may be configured to allow direct manipulation, and accept operator instruction through input directly applied to a link or a joint of the manipulator. The techniques are also applicable to robotic systems that are, in part or in whole, automatically moved.

An operator can manually move an object, e.g., such as part or all of the manipulator assembly 102, by applying a force directly on the object, e.g., using a hand, a foot, or other body part for applying the force directly on the object. The operator can manually or push the object to reposition or reorient the object. In other examples, the operator can manually move the object by interacting with a user input device that causes the object to move. For example, if the object to be manually moved is the manipulator assembly 102, the wheels 112 of the support structure 110, e.g., can be powered wheels that can be controlled by the user input device. In this regard, the manual movement of the manipulator assembly 102 directed by the user device 108 can correspond to manual movement that is generated in response to manual manipulation of a user input device separate from the manipulator assembly 102.

While the setup arm 107 is described as being passive in the above example, in other implementations, the setup arm 107 is an active controllable setup arm. For example, the setup arm can be moved in response to operation of the user input system described herein. In some implementations, the setup arm can be backdriven through operation of a powered joint of the manipulator 103. For example, a distal portion of the manipulator 103 can be fixed, and the powered joint can be operated to backdrive the setup arm, thereby repositioning or reorienting the setup arm.

The support structure 110 is described as including the wheels 112. In some implementations, rather than including wheels, the support structure 110 is mounted in the environment 10 in a manner that enables the support structure 110 to be easily moved in the environment 10. For example, the support structure 110 could be directly mounted to the operating table 105, directly mounted to walls of the environment 10, or directly mounted to a ceiling of the environment 10.

In some implementations, the user device 108 is worn by the operator 106 over the eyes of the operator 106. The user device 108 can be a head-mounted user device, and the display device 124 of the user device 108 can be a see-through display, as described with respect to FIG. 2. In other implementations, rather than being a see-through display device, the display device 124 can be an opaque display device that is substantially opaque to light. The user device 108 as a virtual reality device. To allow the operator 106 to view the environment 10, the sensor 126 of the user device 108 can capture imagery of the environment 10, and the display device 124 can present the imagery of the environment 10. In some cases, the controller 122 can generate imagery of the environment 10 with one or more indicators overlaid on the imagery for guiding the manual movement of the manipulator assembly 102.

While the user device 108 is described as being a head-mounted device with a see-through display, the user device can vary in other implementations. In other implementations, the user device 108 can be carried by the operator 106 in other manners. The user device can be a mobile computing device such as a tablet computer, a smart watch, or a smartphone. For example, the user device 108 can be a smart watch worn on the wrist of the operator 106. The mobile computing device is a handheld computing device that the operator 106 can easily carry around the environment 10 using a hand. Using augmented reality processes, imagery presented on a display device of the mobile computing device can be overlaid on imagery of the environment 10. In this regard, at the operation 504A, 504B, rather than directly overlaying the imagery over the environment 10, the imagery for guiding the manual movement of the manipulator assembly 102 is overlaid on imagery of the environment 10. The imagery of the environment 10 can be captured by an image capture device of the mobile computing device, or an image capture device of another part of the medical system 100.

While a single user device 108 is described with respect to FIGS. 1A and 1B, in other implementations, multiple operators with multiple user devices can be present in the environment 10. The environment 10 includes any number of operators. Referring back to FIG. 4, each of the operators has a corresponding user device 130-1, 130-2, . . . , 130-n (collectively referred to as user devices 130). In some implementations, each of the user devices 130 includes a corresponding display device. The multiple user devices 130 can each include a corresponding display device 134-1, 134-2, . . . , 134-n (collectively referred to as display devices 134). In some implementations, the user devices 130 also include corresponding sensors 136-1, 136-2, . . . , 136-n (collectively referred to as sensors 136). Each of the sensors 136 can be similar to the sensor 126 described with respect to FIG. 3. For example, one or more of the sensors 136 can includes an image capture device. In other implementations, the sensors 136 can include any one of an accelerometer, a motion sensor, a gyroscope, or another type of sensor. In implementations in which multiple user devices 130 are present, the sensor system 137 can include any of the sensors 136 of the multiple user devices 130. In this regard, the controller 122 can receive the data produced by the sensors 136 and use the data for the processes described herein. For example, if the one of the user devices 130 includes a corresponding sensor 136, output from the sensor 136 can be used to provide information that can be used to localize another of the user devices 130, to determine a recommended configuration of the manipulator 103, or to perform other operations described herein.

In the example shown in FIG. 1A, the environment 10 includes four operators 128-1 (i.e., the operator 106), 128-2, 128-3, 128-4 (collectively referred to as operators 128). One or more of the operators 128 can carry a user device. For example, in some implementations, only a portion of the operators 128 in the environment 10 carry user devices. In the example of FIG. 1, the operators 128-1, 128-2, 128-3 each carries a corresponding user device 130-1, 130-2, 130-3. The operator 128-4 operates the user control system 132. One or more of the user devices 130-1, 130-2, 130-3 can include a corresponding sensor. In some cases, each of the user devices 130-1, 130-2, 130-3 includes a corresponding sensor, whereas in other cases, one or two of the user devices 130-1, 130-2, 130-3 includes a corresponding sensor. Similarly, in some cases, each of the user devices 130-1, 130-2, 130-3 includes a corresponding display device, whereas in other cases, one or two of the user devices 130-1, 130-2, 130-3 includes a corresponding display device.

In some implementations, imagery presented on one of the user devices 130 can correspond to imagery captured by one of the other user devices 130. For example, in implementations in which the medical system 100 includes the user device 130-1 carried by the operator 128-1 and the second user device 130-2 carried by the operator 128-2, in the operations 504A, 504B (shown in FIGS. 5A and 5B), imagery presented on the user device 130-1 can correspond to imagery captured by the sensor 136-2 (schematically shown in FIG. 4) of the user device 130-2. If the user device 130-2 is a head-mounted device, the sensor 136-2 of the user device 130-2 can capture imagery of the portion of the environment 10 seen by the operator 128-2. For example, the sensor 136-2 can capture imagery of an equipment table 168 in front of the operator 128-2. In this regard, the display device 134-1 (schematically shown in FIG. 4) of the user device 130-1 can present imagery of the operator 128-2 preparing the equipment on the equipment table 168. In some implementations, the operator 128-1 can operate the user device 130-1 to cause the display device 134-1 to present the imagery being captured by the user device 130-2 of the operator 128-2. This allows the operator 128-1 to easily determine a status of the operator 128-2 or a status of task being performed by the operator 128-2.

In some cases, the display device 134-1 can present an indicator indicative of the status of the operator 128-2 or the status of the task being performed by the operator 128-2. For example, the indicator can indicate that the operator 128-2 is moving a particular piece of equipment, is preparing an instrument for use, or is performing some other operating in preparation for the procedure to be performed on the workpiece. While the user device 130-1 is described as presenting imagery captured by the sensor 136-2 (schematically shown in FIG. 4) of the user device 130-2, in other implementations, the display device 134-2 (schematically shown in FIG. 4) of the user device 130-2 can also or instead present imagery captured by the sensor 136-1 of the user device 130-1. Furthermore, in some implementations, the display device 134-2 can present an indicator indicative of a status of the operator 128-1 or a status of task being performed by the operator 128-1.

In one example, as shown in FIG. 1, the operator 128-1 is moving the manipulator assembly 102, and the operator 128-2 is preparing an instrument for use during the procedure on the patient 104. In such cases, if both the user device 130-1 and the user device 130-2 includes corresponding sensors and display devices. The display device 134-1 of the user device 130-1 can be operated to present an indicator indicative of a status of the equipment preparation being performed by the operator 128-2, and the display device 134-2 of the user device 130-2 can be operated to present an indicator indicative of a status of the manual movement operation being performed by the operator 128-1.

In some implementations, not all of the user devices 130 includes a corresponding sensor or a corresponding display device. For example, the user device 130-1 includes the sensor 136-1 and the display device 134-1, and the user device 130-2 includes the sensor 136-2 but does not include a display device. In such cases, imagery presented on the display device 134-1 is generated based on data generated by the sensor 136-1 and data generated by the sensor 136-2.

In other examples, the user device 130-1 includes the sensor 136-1 and the display device 134-1, and the user device 130-2 includes the display device 134-2 but does not include a sensor. In such cases, the imagery presented by the display device 134-2 can be generated based on data collected by sensors of the sensor system 137 rather than a sensor on the user device 130-2.

In some implementations, if both the user device 130-1 and the user device 130-2 include display devices, the imagery presented by the user device 130-1 and the imagery of the user device 130-2 can be similar to one another. The imagery presented by the user device 130-1 and the imagery of the user device 130-2 can both be overlaid on the environment 10. In some cases, because the user devices 130-1, 130-2 are positioned and oriented differently from one another, the perspective of the imagery presented by the user device 130-1 may differ from the perspective of the imagery presented by the user device 130-2. The imagery presented by the user device 130-1 and the imagery presented by the user device 130-2 can be positioned and oriented relative to a single global reference frame. The user device 130-1 and the user device 130-2 may both present imagery that indicates the path 150 along which the manipulator assembly 102 should be moved. The representation of the path 150 is overlaid over the same portion of the environment 10, e.g., the same portion of the floor surface 20, in both the imagery presented by the user device 130-1 and the imagery presented by the user device 130-2.

In some implementations, the user device 130-1 is operated to guide the manual movement of the manipulator assembly 102, and another user device is operated to guide manual movement of another part of the medical system 100. For example, the user device 130-3 carried by the operator 128-3 can direct a manual movement of an auxiliary system 170 (shown in FIG. 1A). In some implementations, the auxiliary system 170 is a system that provides vision or image processing capabilities to present imagery of, for example, internal anatomy of the patient 104. The user device 130-3 can present imagery that guides the manual movement of the auxiliary system 170 in the environment 10. Other examples of parts for which manual movement can be guided are described herein. The imagery presented on the user device 130-3 can be similar to the imagery described with respect to the user device 108 for guiding the manual movement of the manipulator assembly 102.

In implementations in which the user device 130-1 and the user device 130-2 both include sensors, the sensors 136-1, 136-2 of the user devices 130-1, 130-2 can both detect landmarks in the environment 10 for localizing the user devices 130-1, 130-2. For example, as the user device 130-1 is moved about the environment 10, a first landmark can be extracted from data produced by the sensor 136-1. As the user device 130-2 is moved about the environment 10, a second landmark can be extracted from data produced by the sensor 136-2. The first landmark extracted can correspond to a physical feature in the environment 10 that is distinct from a physical feature corresponding to the second landmark. For example, if the sensors 136-1, 136-2 are image capture devices, the first landmark could correspond to a portion of imagery representing the user control system 132 captured by the sensor 136-1, and the second landmark could correspond to a portion of imagery representing the operating table 105 captured by the sensor 136-2. In other implementations, the landmarks extracted from the data of the sensors 136-1, 136-2 can correspond to the same physical feature in the environment 10. While a first landmark and a second landmark are described, in other implementations, each of the sensors 136-1, 136-2 of the user devices 130-1, 130-2 can collect data from which multiple landmarks are extracted.

In the operation 502A and the operation 502B, position or orientation information are received so that the controller 122 can generate or update the imagery to provide the operator with guidance in manually moving the manipulator 103. A reference frame for the position or orientation information can vary in different implementations. In implementations in which the controller 122 determines a pose of the user device 108, the reference frame for the position or orientation information for the user device 108 can be the same as the reference frame for the position or orientation information for the one or more landmarks. In other implementations, the reference frame for position or orientation information for a landmark differs from the reference frame for position or orientation information for the user device 108.

Figure 6:
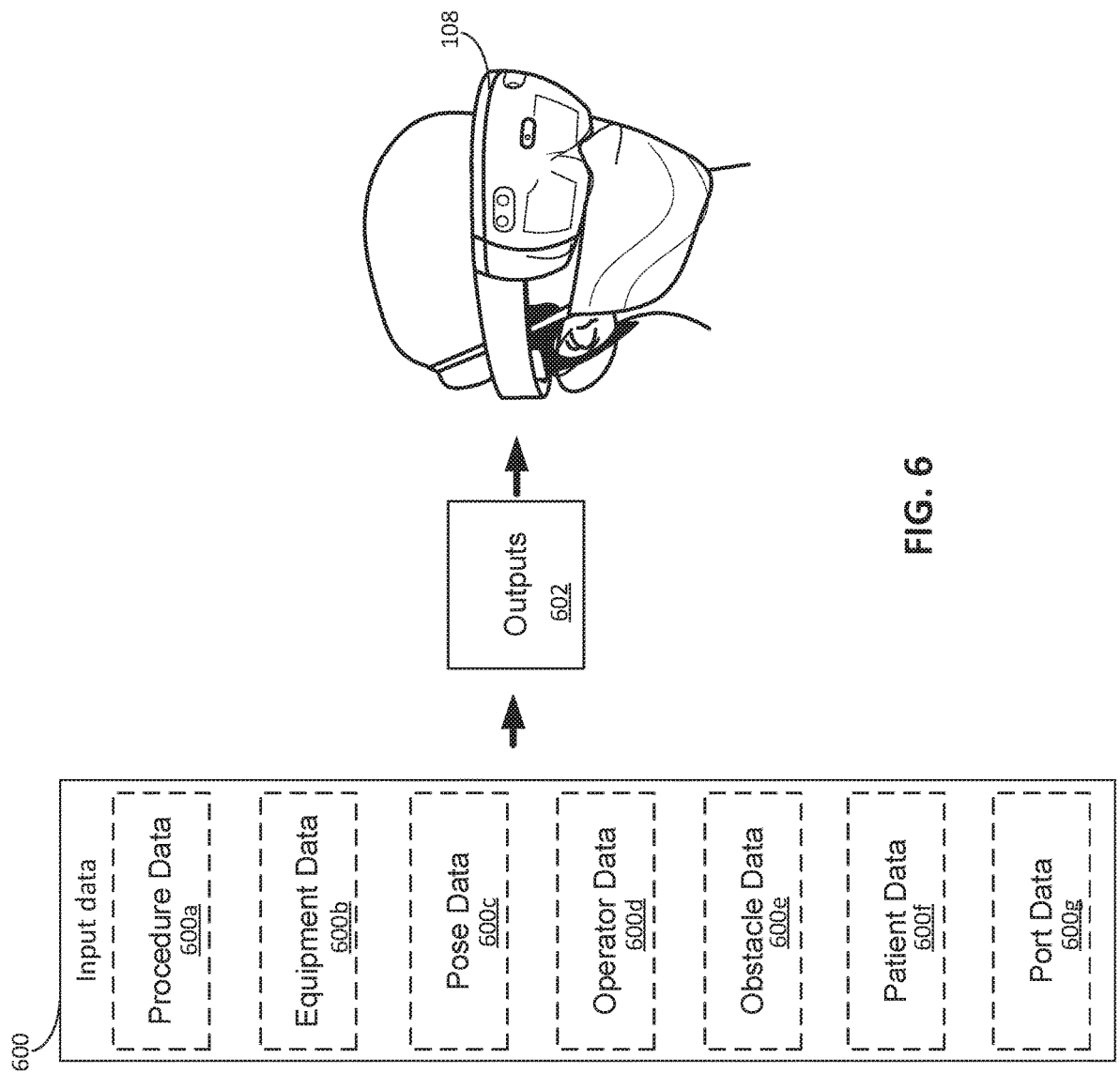
FIG. 6 is a diagram depicting inputs and outputs for a controller performing a process of directing manual movement of a portion of a manipulator assembly.

In some implementations, other information in addition to the position or orientation information can be used to generate or update the imagery. The controller 122 receives, for example, other contextual information pertaining to objects in the environment 10 besides the one or more landmarks. FIG. 6 shows examples of contextual information usable by the controller 122 to generate or update imagery presented on the user device 108. The contextual information can include equipment information, operator information, obstacle information, and patient information. For example, input data 600 are used by the controller 122 to produce an output 602, e.g., signals for causing the user device 108 to present imagery to guide manual movement of the manipulator assembly 102 or a portion thereof. The input data 600 include data loaded into memory associated with the controller 122, user-specified data, data generated by the sensor system 137, etc. The input data 600 include, for example, procedure data 600a, equipment data 600b, pose data 600c, operator data 600d, obstacle data 600e, workpiece data 600f, and port data 600g.

The data 600a, 600b, 600c, 600e, 600f, 600g represent some examples of the data usable by the controller 122 to control the medical system 100 and to generate the imagery presented on the user device 108. Other types and contents of data may be appropriately used by the controller 122 to control the medical system 100 or to control the imagery presented on the user device 108. In addition, while described as input data 600, in some implementations, some data of the input data 600 are generated from other data of the input data 600. Furthermore, while the operation 502A, 502B are described with respect to generating imagery for directing manual movement of a portion of the manipulator assembly 102, the input data 600 can be used for generating imagery to provide other information to the operator 106 as described herein.

The procedure data 600a include data indicative of the specific procedure to be performed. For example, in a medical example, the procedure data 600a include data indicative of the medical procedure to be performed on the patient. In some implementations, an operator selects the type of the procedure before the controller 122 directs the manual movement of the manipulator assembly 102. The controller 122 then generates the imagery presented on the user device 108 based on a type of a medical procedure to be performed by the manipulator 103 of the manipulator assembly 102.

The procedure data 600a can refer to specific requirements of a workspace, such as an area around the workspace that the instrument 116 should be able to access. In one example, the type of the procedure can indicate the specific workspace requirements. The specific type of the procedure may require a predetermined extent of the workspace. In a medical or a surgical example, the workspace can correspond to an area around the patient 104 that the instrument 116 should be able to access during the surgery, due to the specific medical or surgical procedure to be performed on the patient 104.

In another example, the procedure data 600a are generated when the operator selects the extent of the workspace before the manual movement is performed. The operator can select the extent of the workspace in any number of ways. For example, the operator may input the data by highlighting or tracing, on a representation of a workspace presented on a user interface device, a region representative of the desired extent of the workspace. The operator can indicate a boundary of the desired extent of the workspace.

As another example, the desired extent of the workspace can be indicated by prior operator-directed motion of the manipulator 103, e.g., a distal portion of the manipulator 103. An operator can move the manipulator 103 (with or without an instrument being held) to indicate the workspace desired, or by moving a substitute of the instrument 116 to indicate the workspace desired. Example substitutes of the instrument 116 include a device that represents an average instrument that may be used during the procedure, a device that replicates a proximal portion of the instrument 116 but not the entire shaft and end effector, a device that projects a visual indication of locations associated with distal ends of instruments that may be used during the procedure, etc. An image capture device or other sensor can detect the movement of the manipulator 103. If the user interface device corresponds to the user device 108, the sensor 126 of the user device 108 can detect the movement of the manipulator 103. In some implementations, the controller 122 can determine range of motion limits based on signals generated by the sensors associated with the joints 118 of the manipulator 103 when the operator moves the manipulator 103.

Information about a desired setup configuration of the manipulator assembly 102 or the medical system 100 can be derived at least in part from such a demonstration. For example, the desired range of motion of the joints of the manipulator 103 or the instrument 116, and hence the desired location or orientation for the manipulator 103, can be derived at least in part from such a demonstration. Pose sensors of a sensor system 137, for example, can provide data indicative of configurations of the manipulator 103, configurations of the instrument 116, or other system characteristics detectable during the manual demonstration of the desired workspace. The sensor system 137 can thus provide information about the desired range of motion of joints of the manipulator 103 or the instrument 116, or of the desired motion envelope. The controller 122 or other computing system can then process this sensor information to determine the extent of the workspace demonstrated by the operator.

In some implementations, the procedure data 600a can include a plan indicative of a desired or a recommended setup configuration for the manipulator assembly 102 or the medical system 100. For example, the plan can be indicative of positions or orientations of objects in the environment 10. The plan can alternatively or additionally be indicative of desired or recommended locations for one or more objects in the environment 10 for which the controller 122 would direct manual movement, such as the manipulator 103. Alternatively or additionally, the plan can be indicative of known locations of one or more objects in the environment 10, such as equipment for the procedure. The one or more objects can include equipment, landmarks, obstacles, or other objects in the environment 10. The plan, for example, corresponds to a map produced before the controller 122 directs the manual movement of the manipulator 103. An operator can produce the map by interacting with a graphic representation of the environment 10. In a medical example, the operator 106 can indicate a location of an operating table, a patient, medical equipment, or another object that will be in the environment 10 during a medical procedure. The operator can indicate the location using a user input device, e.g., a mouse, a keyboard, or other appropriate user input device. The graphic representation can be presented through the display device 124 of the user device 108. In other implementations, the computing device that the operator uses to produce the plan is independent from the user device 108 worn during the procedure.

In some implementations, the procedure data 600a include a stored plan used for setting up a previous procedure, e.g., a procedure similar to the present procedure. For example, during a previous procedure, the plan used for setting up a medical system or a manipulator assembly is stored to be used for setting up another medical system or manipulator assembly for another procedure.

In one example, the plan is established before any operators are in the environment 10. When the operator 106 begins the preparation process for a medical procedure, e.g., to place the medical system 100 or the manipulator assembly 102 into the setup configuration, a representation of the plan can be presented by the user device 108. The operator 106 can interact with the user device 108 to enter a change into the plan, e.g., updating a location of an object in the environment 10. In examples in which the user device 108 can detect gestures, as described herein, the operator 106 can perform a gesture to update the plan.

The equipment data 600b include data indicative of specifications of the equipment to be used during the procedure. The equipment data 600b can include data that specify a range of motion for each of the joints 118 of the manipulator assembly 102. The range of motion can be a structural or mechanical limitation. In some examples, an initial motion envelope of the instrument 116 is estimated based on initial positions (and/or orientations) of the joints 118 and the ranges of motion of the joints 118 of the manipulator 103. The controller 122 determines recommended positions or orientations for the joints 118 within the ranges of motion that will enable the instrument 116 to achieve a recommended motion envelope for the instrument 116. The controller 122 can drive one or more powered joint of the joints 118 so that the joints 118 move toward the recommended positions or orientations) and the instrument 116 is able to move through the recommended motion envelope.

The equipment data 600b can also include information pertaining to the type of the instrument 116 mounted to the manipulator 103. This information can be produced, e.g., by the instrument sensor 142 (described with respect to FIG. 4). The type of the instrument 116 may affect, for example, an extent of the workspace and an amount of torque necessary to perform an operation. The type of the instrument 116 can be manually inputted by an operator. In some examples, the instrument 116 may include a detectable tag that indicates the type of the instrument 116.

The pose data 600c include data indicative of poses of portions of the medical system 100. The pose data 600c include the position and orientation information received at the operations 502A and 502B. In some implementations, the pose data 600c further include position or orientation information for the manipulator assembly 102 or portions of the manipulator assembly 102, such as the joints 118, the links 120, the instrument holder 114, or other components of the manipulator assembly 102.

The pose data 600c can be indicative of target positions or orientations or actual positions or orientations of portions of the medical system. In one example, the pose data 600c can include information indicative of an actual configuration of the manipulator 103. The pose data 600c, in such cases, can include the initial pose of each of the joints and/or links of the manipulator 103. Alternatively, the pose data 600c can include information indicative of an actual configuration of the manipulator 103 during the guided manual movement of the manipulator 103. The pose of the joints and the links or the configuration of the manipulator 103 can be detected by sensors of the sensor system 137.

In another example, the pose data 600c can include information indicative of a target configuration of the manipulator 103. The target configuration of the manipulator 103 can be determined based on other data and information described herein, or, in some cases, the target configuration of the manipulator 103 can be selected by the operator. In some cases, the target configuration of the manipulator 103 can be indicated on the predefined plan described with respect to the procedure data 600a.

The operator data 600d include data pertaining to the operator(s). In a medical example, the operator data 600d includes data pertaining to the medical team, e.g., the operators 128, carrying out the procedure. The operator data 600d include, for example, information related to the capabilities, preferences for equipment layout, levels of experience, levels of skill, and other operator-specific attributes. In some implementations, the operator data 600d include information related to specific roles for the operators on the medical team. For example, the operator data 600d can include information indicating which operators are equipped to perform tasks requiring sterile handling, e.g., handling medical equipment to be placed into the patient 104. In some examples, an operator profile is created for each of the operators before the procedure. A team profile alternatively or additionally is created for a particular team.

The obstacle data 600e include data indicative of poses (e.g. one or more parameters for positions or orientations) of the patient and obstacles in the environment 10 relative to the manipulator assembly 102. In some examples, the obstacle data 600e can include a map of the environment 10 inputted by the operator. The map can include locations of potential obstacles within the environment 10, such as other pieces of equipment (e.g., of the medical system 100). This map can be similar to the map generated as part of the procedure data 600a.

The obstacle data 600e alternatively or additionally include data from obstacle sensors of the sensor system 137. The obstacle sensor 144 can generate signals indicative of positions, orientations, or poses of obstacles within the environment 10 before the procedure, or as the manipulator 103 moves about the environment 10 during the procedure.

While the chair 158 is described as one example of a potential obstacle with which the manipulator assembly 102 could collide, other examples are possible. In some implementations, potential obstacles include the operating table 105, the auxiliary system 170, another manipulator assembly, a human operator, the user control system 132, or other fixtures in the environment 10.

In some medical contexts, the workpiece data 600f include patient data and include data indicative of patient-specific characteristics. Such patient data can include data indicative of patient body habitus and patient geometry. In some examples, the operator inputs the data indicative of the patient habitus and the patient geometry. In some cases, an imaging device can produce images that can be analyzed by the controller 122 (or by a computational system prior or during a procedure) to determine the patient habitus and the patient geometry. The imaging device may include part of the instrument 116. In some examples, the workpiece data 600f can also include data indicative of the pose of the patient relative to the manipulator 103 and/or the pose of the operating table 105 relative to the manipulator 103. The workpiece data 600f can include pre-operative images, such as x-ray images, x-ray computed tomography images, magnetic resonance imaging scans, and the like. In some cases, the workpiece data 600f includes intraoperative images or surface scans. A portion of the workpiece data 600f can be produced by the patient sensor 140.

The port data 600g include data indicative of characteristics of an access port. In medical implementations, the access port corresponds to a device inserted through a body wall of the patient 104 through which a portion of the medical system 100 can be inserted to access anatomy of the patient 104. The access port, for example, provides a conduit through which the instrument 116 is inserted to access the anatomy of the patient 104. In one example, the port data 600g can indicate a recommended position or orientation of the access port. The recommended position or orientation of the access port can be indicated on the predefined plan described with respect to the procedure data 600a. In some implementations, the recommended position or orientation of the access port is based on a pose of the manipulator 103 when a cannula coupled to the manipulator 103 is docked, when an operator indicates readiness for repositioning of the base 111, when an instrument 116 is mounted, etc. In some medical implementations, a component such as the instrument 116 is inserted through the access port on the patient, and the controller 122 can determine the position and orientation of the access port based on signals from sensors on the manipulator 103.

In another example, the port data 600g can indicate an actual position or orientation of the access port. The actual position or orientation of the access port can be detected by sensors of the sensor system 137. For example, the sensor 126 of the user device 108 can detect the position or orientation of the access port. The controller 122 can direct the manual movement of the manipulator 103 based on the recommended or actual position or orientation of the access port so that an instrument held by the instrument holder 114 of the manipulator 103 can be easily inserted into the access port.

As described with respect to the procedure data 600a, the operator 106 can specify the procedure data 600a or portions of the procedure data 600a before the controller 122 directs the manual movement of the manipulator assembly 102. And, as described with respect to the procedure data 600a and the obstacle data 600e, the operator 106 can specify locations of objects in the environment 10. In some implementations, the operator 106 can specify other types of the input data 600. For example, in some implementations, the operator 106 can specify the equipment data 600b by specifying the types of equipment that will be used during the procedure. The operator 106 can also specify specifications of the equipment. In another example, the operator 106 can specify the characteristics of the operators that would be participating in the procedure and hence specify the operator data 600d.

For portions of the input data 600 that are specified by the operator 106, the operator 106 can interact with a computing device to specify the data, e.g., a personal computer, a tablet computing device, a mobile phone, the user device 108, or other computing device. In some implementations, the operator 106 provides a user input by performing a gesture detectable by the sensor 126 of the user device 108. For example, the sensor 126 is positioned to detect movement of the operator 106, and the controller 122 can direct the manual movement of the manipulator 103 in response to the detected movement. The controller 122 can be configured to detect predefined operator gestures that cause the controller 122 to perform corresponding operations.

In some examples, the imagery presented on the user device 108 includes one or more indicators, e.g., indicative of potential positions for objects, indicative of guidance for moving the manipulator 103, indicative of an alert or alarm, or indicative of other information relevant to the operator 106. An indicator in the imagery can be updated, e.g., repositioned in the imagery, cleared from the imagery, adjusted to provide additional details, or adjusted in some other manner, in response to a gesture performed by the operator 106. The controller 122 can update the imagery in response to the gesture being proximate to or directed toward the indicator.

In one example, the controller 122 causes the user device 108 to stop presenting imagery when the operator 106 performs a broad swiping motion from one side to another side of the viewing frame of the user device 108.

In another example, the user device 108 can present imagery indicative of waypoints 156 for a recommended path 150 of movement for the manipulator assembly 102. The operator 106 can perform a gesture directed toward one of the waypoints 156. For example, the operator 106 can extend a hand toward the waypoint and the move the hand in a direction to manually move the waypoint. In particular, in response to the gesture, the user device 108 updates the imagery such that the waypoint is repositioned in the direction indicated by the gesture of the operator 106. In some examples, as described with respect to FIGS. 1A and 1B, the imagery can include an indicator of a target location for the manipulator assembly 102. Rather than causing waypoint to be repositioned, the operator 106 performs a gesture to cause the target location of the manipulator assembly 102 to be repositioned at a new target location.

In a further example, the operator 106 can perform gestures to rearrange the graphic representation of objects in the environment 10 as described with respect to the procedure data 600a. If the graphic representation of the environment 10 is presented through a see-through display on the user device 108, the see-through display can present imagery including a representation of an object that would be in the environment 10 during the medical procedure. A gesture performed by the operator 106 can be indicative of the location of the object during the procedure. The user device 108 updates the imagery to indicate the location of the object. In some cases, the location of the object is indicated in the imagery, the gesture performed by the operator 106 can cause the user device 108 to update the imagery to indicate a new location of the object. In some examples, the objects correspond to the equipment to be used during the procedure. The imagery includes graphic representations of various pieces of equipment, such as a Mayo stand, an accessory cart, a medical imaging system, or other equipment that could be used during the procedure. For pre-operative planning purposes, the operator 106 performs gestures to create the plan indicative of the locations of the various pieces of equipment, and, as described herein, the controller 122 updates the imagery based on these gestures. The controller 122 can further direct the manual movement of the manipulator 103 based on this plan.

In some implementations, the user device 108 presents imagery to direct the manual movement of the manipulator 103, and the operator 106 performs a gesture to indicate a location of a piece of equipment that will be placed in the environment 10. Based on this indicated location, the controller 122 can update the imagery so that the guidance provided by the imagery accounts for the piece of equipment to be placed in the environment 10.

While the operator 106 can provide user inputs that the controller 122 uses to control the imagery presented through the user device 108, in some implementations described herein, sensors of the sensor system 137 produce portions of the input data 600 used by the controller 122 to present the imagery. For example, as described with respect to the pose data 600c, sensors of the sensor system 137 can detect positions and orientations of portions of the medical system 100. In some implementations, the controller 122 can receive information from both the sensor 126 of the user device 108 and another sensor of the sensor system 137. The information provided by the other sensor can also be indicative of a position or orientation of the one or more landmarks detected by the sensor 126 of the user device 108. Alternatively or additionally, the information can be kinematic information for the manipulator 103 or kinematic information for another portion of the medical system 100. The controller 122 can cause the user device 108 to present the imagery overlaid in the environment based on this received kinematic information.

In one example, the other sensor is a sensor of another user device worn by another operator in the environment 10. For example, the other sensor is a sensor of one of the user device 130 worn by one of the operators 128. In another example, the other sensor is a sensor mounted to the environment 10, such as an image capture device mounted to a wall surface, a floor surface, or some other portion of the environment 10. The image capture device can be fixed in the environment 10 or can be mounted to a movable object within the environment 10. In some cases, the image capture device is part of equipment of the medical system 100. In further examples, the other sensor is an integrated portion of the medical system 100. For example, the other sensor can correspond to a joint sensor of the manipulator assembly 102.

In implementations in which multiple operators 128 are present in the environment 10, the different operators 128 can collaboratively provide or update input data 600. For example, if the first operator 128-1 and the second operator 128-2 are both carrying user devices 130-1, 130-2, the first user device 130-1 and the second user device 130-2 can both present imagery indicative of the plan (described with respect to the procedure data 600a) for different objects in the environment 10. For example, the imagery can include graphical representations of the objects overlaid in the environment 10 such that the operators 128-1, 128-2 can easily manually move the real world objects to coincide with the graphical representation of the objects. The first and second operators 128-1, 128-2 can reposition and reorient objects in the environment based on the predefined plan, e.g., by independently moving different objects in the environment 10 to their planned positions.

The first user device 130-1 and the second user device 130-2 can provide the guidance for manual movement of the objects as described herein. In further implementations, the first and second operators 128-1, 128-2 can collaboratively update the plan. For example, the first and second operators 128-1, 128-2 can operate user input devices as described herein, e.g., operating a touchscreen or performing a gesture, to select a new desired position or orientation of an object in the environment 10. The graphic representation of the object is accordingly repositioned or reoriented to reflect the newly selected position or orientation in both the imagery presented by the first user device 130-1 and the imagery presented by the second user device 130-2. If the second operator 128-2 selects a new desired position or orientation for the equipment table 168, the graphic representations of the equipment table 168 in both the imagery presented by the first user device 130-1 and the imagery presented by the second user device 130-2 are updated.

In the operation 504A and the operation 504B, imagery is presented through the display device 124 of the user device 108. As described herein, the imagery can be presented to direct the operator 106 to reposition or to reorient the manipulator assembly 102 or a portion of the manipulator assembly 102. While the imagery is described as presenting a path 150 along which the manipulator assembly 102 should be moved, in other examples, the imagery presents other types of indicators to direct the manual movement of the manipulator assembly 102. For example, the imagery can include an indicator indicative of a direction in which the manipulator assembly 102 should be manually translated by the operator 106.

In examples in which the operator 106 is directed to reorient the manipulator assembly 102 or a portion of the manipulator assembly 102, the user device 108 can present imagery including an alignment indicator. For example, if the controller 122 directs reorientation of the manipulator 103, the alignment indicator be a line, a mark, or other indicator indicative of a target orientation of a link or a joint of the manipulator 103.

The imagery presented by the display device 124 is described as being overlaid in the environment 10. If the display device 124 is part of a head mounted user device worn over the eyes of the operator 106, the imagery presented on the display device 124 is positioned between the environment 10 and the display device 124 such that the imagery is overlaid on the environment 10 as seen by the operator 106. In some implementations, the user device 108 presents imagery that portions of the environment overlay. For example, if the user device 108 is a tablet computer, a smart phone, or other device that can have an opaque display, the opaque display can present captured imagery of the environment 10 with additional imagery or an indicator separate from the captured imagery of the environment 10. The additional imagery may include content similar to the content described with respect to the imagery presented by the user device 108. In some examples, the additional imagery is presented so as to appear overlaid on the captured imagery of the environment 10.

In some implementations, a portion of the captured imagery of the environment 10 appears to overlay the additional presented imagery. For example, referring back to FIG. 1A, the operating table 105 is positioned between the operator 106 and the auxiliary system 170. If the user device 108 presents an indicator indicative of a location of the auxiliary system 170, the user device 108 can present the indicator such that the operating table 105 appears to be overlaid on the indicator. The indicator can be partially overlaid by the operating table 105.

Figure 7A:
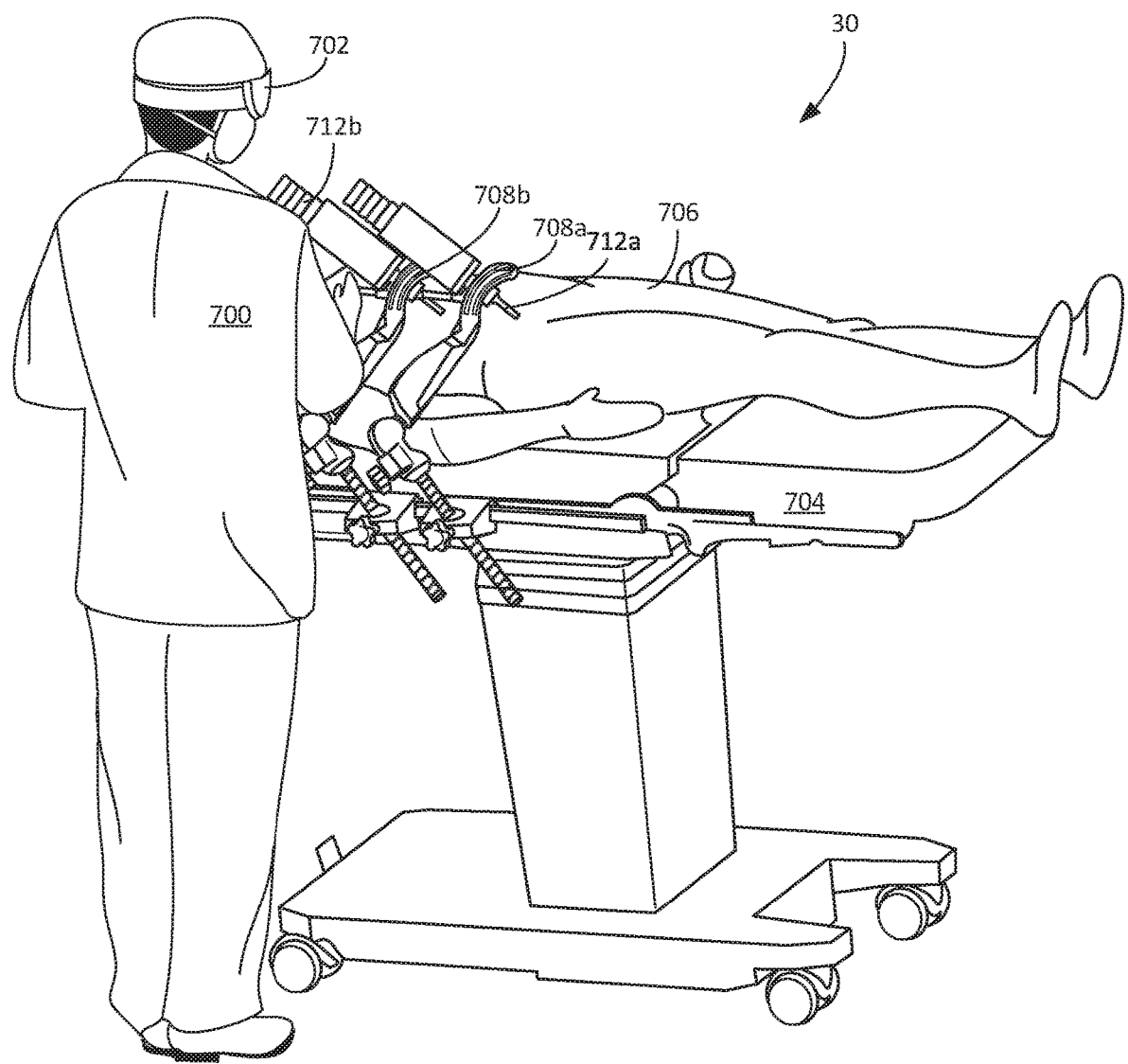
FIG. 7A is a perspective view of another example of a surgical environment with a robotic device and an operator.
Figure 7B:
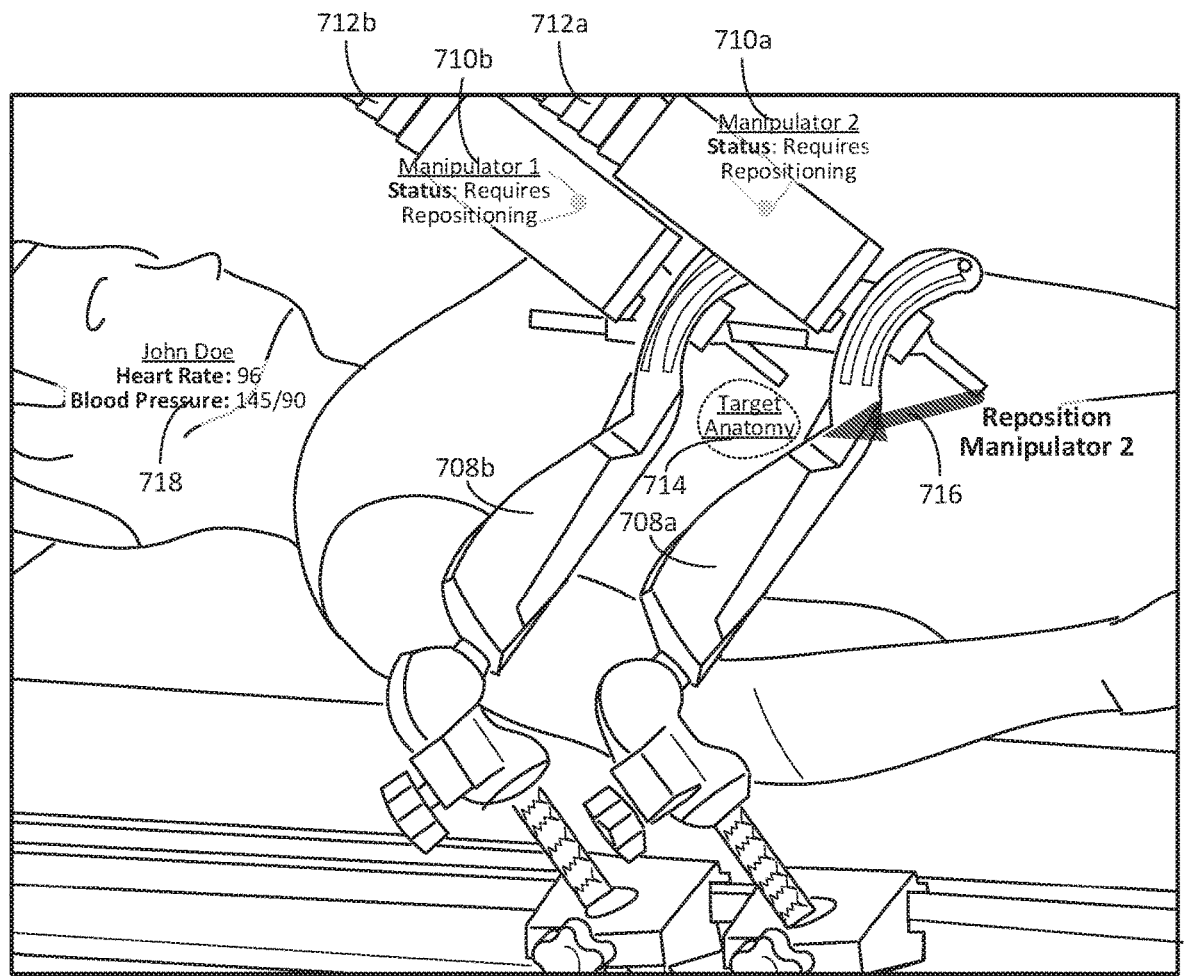
FIG. 7B is a perspective view of the surgical environment including a depiction of imagery in the environment presented to an operator through a user device.

The imagery can be indicative of information other than guidance for manual movement of the manipulator assembly 102 or a portion thereof. FIGS. 7A and 7B depict another example of imagery that could be presented by a head mounted user device. Referring to FIG. 7A, an operator 700 wearing a user device 702 (e.g., similar to the user device 108) is positioned in an environment 30 proximate an operating table 704 supporting a patient 706. Manipulators 708a and 708b are mounted on the operating table 704.

FIG. 7B depicts an example of imagery overlaid in the environment 30 that the user device 702 presents to the operator 700. The imagery includes status indicators 710a, 710b for the manipulators 708a, 708b. In the example shown in FIG. 7B, the status indicators 710a, 710b are indicative of whether the manipulators 708a, 708b require manual repositioning. In other implementations, the status indicators 710a, 710b are indicative of whether the manipulators 708a, 708b require manual reorienting or both manual repositioning and manual reorienting. In the example shown in FIG. 7B, the imagery includes a directional indicator 716 indicative of a direction that the manipulator 708b should be moved.

In some examples, the manual movement of the manipulator 708b is before any portion of a medical procedure has performed on the patient 706. For example, the manual movement can be directed before an access port has been inserted into the patient 706, and before instruments 712a, 712b have been inserted into the patient 706. In other examples, the manual movement of the manipulator 708b is directed after a portion of the medical procedure has been performed. For example, the manual movement of the manipulator 708b is directed after the instrument 712b has been inserted into the patient 706. The instrument 712b is retracted from the patient 706, and the user device 702 presents the imagery to direct the manual movement of the manipulator 708b to a new position or orientation.

Such repositioning or reorienting after the medical procedure has been initiated but before the medical procedure has been completed can be necessary to complete the medical procedure. For example, a first stage of the medical procedure can require that the instruments 712a, 712b be used on a first region of a target anatomy, and a second stage of the medical procedure can require that the instrument 712a, 712b be used on a second region of the target anatomy. The manual repositioning of the manipulator 708b and manual repositioning of the manipulator 708a can be initiated when the first stage of the medical procedure is complete. The manipulators 708a, 708b can be repositioned or reoriented so that they can access the second region of the target anatomy.

In some implementations, rather than being indicative of whether the manipulators 708a, 708b need to be moved, the indicators 710a, 710b are indicative of other conditions of the manipulators 708a, 708b. For example, the indicators 710a, 710b could be indicative of whether the manipulators 708a, 708b are operational or whether the manipulators 708a, 708b have been properly mounted to the operating table 704. In some examples, the indicators 710a, 710b are indicative of a condition or status of instruments 712a, 712b mounted to the manipulators 708a, 708b. For example, the indicators 710a, 710b could be indicative of types of the instruments 712a, 712b that are currently mounted to the manipulators 708a, 708b, durations that the instruments 712a, 712b have been used, or whether the instruments 712a, 712b should be replaced with new instruments.

The example imagery of FIG. 7B further includes an anatomy indicator 714 indicative of a region corresponding to target anatomy to be accessed by the instruments 712a, 712b. The anatomy indicator 712 can include a representation of an internal anatomy of the patient 706 such that the operator 700 can easily move the manipulators 708a, 708b relative to the internal anatomy that would typically not be visible to the operator 700 without a separate medical imaging system. The anatomy indicator 712, particularly in implementations in which the user device 702 is worn over eyes of the operator 700, can be generated based on imagery captured by the medical imaging system. For example, the anatomy indicator 712 can be a graphic representation of the internal anatomy of the patient 706 present in imagery captured by the medical imaging system.

In other implementations, the imagery can include anatomy indicators indicative of regions corresponding to anatomical features not to be accessed by the instruments 712a, 712b. These anatomy indicators can indicate regions that the operator 700 should avoid when moving the manipulators 708a, 708b.

In further implementations, the imagery can include a patient indicator 718 indicative of a status of the patient 706. For example, the patient indicator 718 can indicate a heart rate and a blood pressure of the patient 706. The patient indicator 718 can be generated based on the input data 600 described with respect to FIG. 6, e.g., the workpiece data 600f.

The examples of FIGS. 1A and 1B depict one example of depicting guidance of manual movement of the manipulator assembly 102. For example, in FIGS. 1A and 1B, the imagery indicates the path 150 for directing the manual movement of the manipulator assembly 102. In other implementations, the imagery indicates multiple selectable paths along which the manipulator assembly 102 should be moved. Each of the selectable paths directs the manipulator assembly 102 from its current location to the desired or recommended location.

In the examples shown in FIGS. 1A and 1B, the path 150 is shown as including multiple waypoints 156. In some implementations, the path 150 corresponds to a region through which the manipulator assembly 102 should be moved to move the manipulator assembly 102 from its current location to its desired or recommended location. The region can be larger than the area footprint of the manipulator assembly 102 or the area footprint of the support structure 110 of the manipulator assembly 102. The region defines boundaries within which the support structure 110 of the manipulator assembly 102 should be kept to avoid obstacles in the environment 10. The manipulator assembly 102 could be moved along any one of multiple paths through the region.

In some implementations, in addition to or rather than presenting a representation of a path of desired or recommended movement for the manipulator assembly 102, the user device 108 presents an indicator indicative of a desired or recommended direction of motion for the manipulator assembly 102. As the operator 106 moves the manipulator assembly 102 in the desired or recommended direction, the desired or recommended direction of motion indicated by the indicator is updated so that the operator 106 can move the manipulator assembly 102 to the desired or recommended location. Additionally or alternatively, the indicator can be indicative of a desired or recommended magnitude of movement for the manipulator assembly 102. For example, the indicator can include text specifying a distance that the manipulator assembly 102 should be moved. In examples in which the indicator is a directional arrow, the size of the directional arrow could be indicative of the amount of movement that the manipulator assembly 102 should be moved in the indicated direction.

While the indicator 160 is described as being presented proximate an obstacle near the path 150 in FIG. 1B, in some implementations, an indicator presented by the user device 108 is indicative of a location of the obstacle but is not necessarily proximate to the obstacle. For example, the user device 108 can present an annotation indicative of a direction of an obstacle as the operator 106 moves the manipulator assembly 102 along the path 150. For example, the annotation include an indicator in the form of a directional arrow that indicates that an obstacle is in a particular direction.

In the examples described with respect to FIGS. 1A and 1B, the manipulator assembly 102 and its manipulator 103 are described as being manually moved in accordance with indications presented by the user device 108. The user device 108 can present imagery to guide manual movement of other parts of the medical system 100 or other portions of the manipulator assembly 102 in certain implementations. For example, in some implementations, the user device 108 presents imagery to guide manual movement of the base 111 of the manipulator 103, the support structure 110 of the manipulator assembly 102, or the instrument holder 114 of the manipulator 103. In further implementations, manual movement of an intermediate portion of the manipulator 103 is guided. For example, the user device 108 can present imagery to direct manual movement of a particular one of the joints 118 or a particular one of the links 120. In other implementations, manual movement of a distal portion of the manipulator assembly 102 or a proximal portion of the manipulator assembly 102 is directed. For example, the user device 108 can present imagery to guide manual movement of the instrument holder 114 to direct manual movement of the distal portion of the manipulator assembly 102, and the user device 108 can present imagery to direct manual movement of the column 109 or the support structure 110 to direct manual movement of the proximal portion of the manipulator assembly 102.

In some examples, the imagery presented includes a representation of a configuration for the manipulator 103 recommended by the controller 122 based on the input data 600. The representation of the recommended configuration for the manipulator 103 can be indicative of a recommended orientation, a recommended position, or both a recommended orientation and a recommended position of one or more of the joints 118, one or more of the links 120, the base 111, or a combination thereof. The representation of the recommended configuration can correspond to imagery overlaid on the environment 10. In some implementations, the representation is an opaque, or a partially transparent, graphic representation of the manipulator 103 in the recommended configuration.

In some examples, the imagery provides an animation of a recommended motion of the manipulator 103 to the recommended orientation, recommended position, or recommended pose. The animation can be indicative of a sequence of positions or orientations between the current position and orientation of the manipulator 103 and the recommend position and orientation of the manipulator 103. In some cases, the animation can provide a representation of a manner of movement of the operator to manually move the manipulator 103 into the recommended position or orientation. For example, the animation can represent hands of the operator and the recommended motion of the hands to manually move the manipulator 103. The animation can include one or more transparent graphic representations of the manipulator 103 or the operator overlaid on the environment.

In some implementations, rather than directing manual movement of a portion of the manipulator assembly 102, the user device 108 presents imagery to direct manual movement of another part of the medical system 100. In some implementations, the imagery is presented to direct manual movement of the instrument 116 mounted to the manipulator 103 or a cannula through which the instrument 116 is inserted. In implementations in which an access port is inserted through a body wall of the patient 104, the imagery presented by the user device 108 can be indicative of a desirable or undesirable locations of the access port. The imagery can indicate a recommended port location where the access port should be manually placed by the operator 106. The recommended port location corresponds to a recommendation determined by the controller 122 based on the input data 600. In other implementations, the imagery can indicate a keep out region indicative of locations that the access port should not be placed.

The user device 108 can direct manual movement of other parts of the medical system 100. In some implementations, the user device 108 presents imagery to direct manual movement of another manipulator assembly in accordance with implementations described herein with respect to directing manual movement of the manipulator assembly 102 and portions thereof. This other manipulator assembly is distinct from the manipulator assembly 102. In some implementations, this other manipulator assembly is separate from the manipulator assembly 102. The manipulator assembly 102 and the other manipulator assembly are standalone assemblies each including its own separate support structure. In other implementations, the manipulator assembly 102 and the other manipulator assembly share a common support structure movable about the environment 10.

In other implementations, additionally or alternatively, the user device 108 presents imagery to direct manual movement of an auxiliary system of the medical system 100. The auxiliary system includes a resource such as, an illumination source, an energy source, an insufflation source, an instrument storage component, a central processor, or a combination thereof. The auxiliary system can be a standalone system movable about the environment 10. For example, the auxiliary system can correspond to a medical imaging system, the user control system 132, the equipment table 168, an insufflation system (not shown in FIG. 1A), the operating table 105, or other system in the environment 10. Other auxiliary systems for which manual movement could be directed include trays, tables, imaging systems, user consoles, surgical instruments, medical instruments, diagnostic instruments, or other equipment. The features of the implementations described herein for directing manual movement of the manipulator assembly 102 can also be features of implementations in which the imagery presented is for directing manual movement of the auxiliary system. By presenting imagery to direct manual movement of an auxiliary system, the user device 108 enables an operator to easily set up equipment relative to the manipulator assembly 102 or relative to other equipment in the environment 10.

In some implementations, the user device 108 presents imagery to direct movement of the patient 104 in the environment 10. For example, the operating table 105 on which the patient 104 is supported can be moved to move the patient 104 about the environment 10. In other implementations, the user device 108 presents imagery to direct movement of an operator in the environment 10. For example, in implementations in which the environment 10 includes the first operator 128-1 and the second operator 128-2, the user device 130-1 worn by the first operator 128-1 can direct movement of the first operator 128-1, the second operator 128-2, or both. Similarly, the user device 130-2 worn by the second operator 128-2 can direct movement of the first operator 128-1, the second operator 128-2, or both. Desirable locations of the first and second operators 128-1, 128-2 can be determined based on the operator data 600d as well as different types of position and orientation information described herein, e.g., for obstacles, the manipulator assembly 102, and other objects in the environment 10. In implementations in which the operator data 600d include information related to whether an operator is equipped to handle sterile equipment, this information can be used to determine the task that the operator should perform in the environment and a location to perform the task. For example, the information may indicate that the first operator 128-1 is not equipped to handle sterile equipment, and hence the first operator 128-1 is directed to manually move the manipulator assembly 102. In contrast, the operator 128-2 is equipped to handle sterile equipment and hence is directed to prepare instruments for insertion into the patient 104. The operator 128-2 could also be directed to be at the bedside of the patient 104 to perform tasks proximate the patient 104, such as pointing out locations for the access port or for insertion of the instrument 116 (shown in FIG. 2).

As described herein, the techniques, systems, and methods described herein can be used to reposition or reorient a portion of the manipulator assembly or a portion of the medical system before a medical procedure is performed (e.g., pre-operative repositioning or reorienting) or during the medical procedure (e.g., intra-operative repositioning or reorienting). For example, during the medical procedure, these techniques, systems, and methods can be used to reposition or reorient a portion of the manipulator assembly or a portion of the medical system in response to an emergency condition, e.g., a patient condition or an equipment condition that requires the medical system or the manipulator assembly to be placed into a new configuration. In other implementations, the techniques, systems, and methods can be used after the medical procedure to facilitate take-down of the manipulator assembly or the medical system.

The systems (e.g., the medical system 100) and robotic components of the medical systems (e.g., the manipulator 103) described herein can be computer-assisted systems. For example, each of these systems and robotic components can be controlled, at least in part, using one or more computer program products, e.g., one or more computer programs tangibly embodied in one or more information carriers, such as one or more non-transitory machine-readable media, for execution by, or to control the operation of, one or more data processing apparatus, e.g., a programmable processor, a computer, multiple computers, and/or programmable logic components. The systems and robotic components can be controlled using a single computer program product or multiple distinct computer program products for distinct systems and robotic components. A computer program, e.g., for the one or more computer program products, can be written in any form of programming language, including compiled or interpreted languages, and it can be deployed in any form, including as a standalone program or as a module, component, subroutine, or other unit suitable for use in a computing environment.

Operations associated with controlling the medical systems described herein can be performed by a controller (e.g., the controller 122). The controller can include one or more programmable processors executing one or more computer programs to perform the functions described herein. The one or more programmable processors can includes multiple processors that are part of distinct subsystems in the medical system 100, e.g., a processor of the manipulator assembly 102, a processor of the user control system 132, a processor of the auxiliary system 170, and/or another processor of the medical system 100. In other implementations, the one or more programmable processors can include one or more processors that are remote from the environment 10, e.g., a processor of a remote server. Control over all or part of the medical systems described herein can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

What is claimed is:

1. A computer-assisted medical system comprising:
   a user device wearable by an operator, the user device comprising:
      a display device configured to present imagery overlaid in an environment of a manipulator assembly, and
      a sensor configured to detect one or more landmarks in the environment; and
   a controller configured to execute instructions to perform operations, the operations comprising:
      receiving, from the sensor, position or orientation information for the one or more landmarks in the environment, and
      directing a manual movement of a portion of the manipulator assembly by causing the display device to present guidance for performing the manual movement within the imagery overlaid in the environment based on the received position or orientation information, wherein:
         causing the display device to present the imagery comprises causing the display device to present the imagery overlaid with a floor surface in the environment to direct the manual movement of the portion of the manipulator assembly along the floor surface, or the imagery indicates a path from a current location of the portion of the manipulator assembly toward a recommended location of the portion of the manipulator assembly.

2. The medical system of claim 1, wherein the operations further comprise:
directing a manual movement of a portion of the medical system relative to the manipulator assembly by causing the display device to present the imagery overlaid in the environment based on the received position or orientation information, the portion of the medical system being distinct from the manipulator assembly.

3. The medical system of claim 1, wherein:
the imagery is first imagery, and
the operations further comprise directing a manual movement of a patient relative to the manipulator assembly by causing the display device to present second imagery overlaid in the environment based on the received position or orientation information.

4. The medical system of claim 1, wherein:
the operations further comprise receiving user input information and determining a recommended configuration based on the user input information, and
directing the manual movement comprises directing the manual movement further based on the recommended configuration.

5. The medical system of claim 1, wherein:
directing the manual movement of the portion of the manipulator assembly comprises directing a user to reorient the portion of the manipulator assembly relative to an alignment indicator in the imagery; or
the imagery overlaid in the environment is indicative of one or more waypoints for the manual movement of the portion of the manipulator assembly.

6. The medical system of claim 1, wherein the imagery overlaid in the environment comprises a map having a first region indicative of undesirable locations for the portion of the manipulator assembly or indicative of desirable locations for the portion of the manipulator assembly.

7. The medical system of claim 1, wherein the imagery overlaid in the environment comprises:
a map having a first region indicative of desirable locations for the portion of the manipulator assembly and a second region indicative of undesirable locations for the portion of the manipulator assembly; or
a map indicative of a desirability value for each location of a plurality of locations; or
an annotation indicative of a direction of motion or a magnitude of motion toward a desirable location for the portion of the manipulator assembly.

8. The medical system of claim 1, wherein the imagery further comprises an indicator of an obstacle along the floor surface or proximate the path.

9. The medical system of claim 1, wherein the imagery:
indicates a recommended port location for a manipulator of the manipulator assembly, or indicates a keep out region for the manipulator assembly, or indicates a recommended configuration of the manipulator assembly, or comprises a representation of an internal anatomy of a patient.

10. The medical system of claim 1, wherein:
the operator is a first operator,
the user device is a first user device wearable by the first operator,
the display device is a first display device,
the imagery is first imagery,
the one or more landmarks are one or more first landmarks, and
the medical system further comprises a second user device wearable by a second operator, the second user device comprising a second display device configured to present second imagery overlaid in the environment of the manipulator assembly, and a second sensor configured to detect one or more second landmarks in the environment, and
the operations further comprise causing the second display device to present the second imagery overlaid in the environment based on a same reference frame as used for causing the first display device to present the first imagery.

11. The medical system of claim 1, wherein:
the operator is a first operator,
the user device is a first user device,
the imagery is a first imagery, and
the operations further comprise causing the display device of the first user device to present second imagery captured by a second user device worn by a second operator.

12. The medical system of claim 1, wherein:
the operator is a first operator,
the user device is a first user device,
the medical system comprises a plurality of user devices, the plurality of user devices comprising the first user device and a second user device wearable by a second operator,
the imagery is a first imagery, and
the operations further comprise directing manual movement of a part of the medical system distinct from the manipulator assembly by causing a second display device of the second user device to present second imagery overlaid in the environment.

13. The medical system of claim 1, wherein:
the sensor is configured to detect movement of a user, and
directing the manual movement of the portion of the manipulator assembly comprises directing the manual movement of the portion of the manipulator assembly based on the detected movement of the user.

14. The medical system of claim 13, wherein the operations further comprise determining a desired setup configuration for the medical system based on the detected movement of the user.

15. The medical system of claim 1, wherein:
the sensor is configured to detect a user gesture, and
the operations further comprise updating the imagery in response to the user gesture,
the imagery comprises an indicator overlaid in the environment at a first target location for the portion of the manipulator assembly, and
updating the imagery comprises updating the imagery such that the indicator is moved relative to the environment in response to the user gesture.

16. The medical system of claim 1, wherein:
the sensor is configured to detect an actual port location,
the operations further comprise updating the imagery in response to the actual port location.

17. The medical system of claim 1, wherein the operations further comprise:
based on updated position or orientation information for the one or more landmarks, updating the imagery to direct an updated manual movement of a portion of the manipulator assembly; or causing the display device to present the imagery further based on a kinematic configuration of a manipulator assembly.

18. The medical system of claim 1, wherein the operations comprise:
before directing the manual movement, generating the imagery based on prior user-directed motion of the manipulator assembly, generating the imagery based on a type of a medical procedure to be performed by the manipulator assembly, generating the imagery based on a target or actual location of a port on a patient, or generating the imagery based on a target or actual configuration of the manipulator assembly, or generating the imagery based on a predefined plan indicative of recommended positions or orientations of the one or more landmarks in the environment.

19. The medical system of claim 1, wherein:
the operations further comprise receiving contextual information, the contextual information selected from the group consisting of: equipment information, operator information, obstacle information, and patient information, and
directing the manual movement comprises directing the manual movement further based on the contextual information.

20. The medical system of claim 1, further comprising:
the manipulator assembly, wherein the manipulator assembly comprises a teleoperated manipulator; and
an input device for receiving user commands to move the teleoperated manipulator.

21. A method of setting up a computer-assisted medical system comprising a manipulator assembly, the method comprising:
receiving, from a sensor of a user device of the computer-assisted medical system, position or orientation information for one or more landmarks in an environment, and
directing a manual movement of a portion of the manipulator assembly by causing a display device of the user device to present guidance for performing the manual movement within imagery overlaid in the environment based on the received position or orientation information, wherein:
causing the display device to present the imagery comprises causing the display device to present the imagery overlaid with a floor surface in the environment to direct the manual movement of the portion of the manipulator assembly along the floor surface, or
the imagery indicates a path from a current location of the portion of the manipulator assembly toward a recommended location of the portion of the manipulator assembly.

22. The method of claim 21, further comprising:
directing a manual movement of a portion of the medical system relative to the manipulator assembly by causing the display device to present the imagery overlaid in the environment, the portion of the medical system being distinct from the manipulator assembly.

23. The method of claim 22, wherein the imagery overlaid in the environment comprises:
a first region indicative of undesirable locations for the portion of the manipulator assembly; or
a second region indicative of desirable locations for the portion of the manipulator assembly; or
a desirability value for the portion of the manipulator assembly in each location of a plurality locations in the environment.

24. The method of claim 21, further comprising:
creating the imagery based on data comprising information selected from the group consisting of: a target location of a port for an entry by the manipulator assembly, an actual location of the port, procedure information, equipment information, operator information, obstacle information, patient information, and a predefined plan for a medical procedure to be performed by the manipulator assembly.

25. A non-transitory machine-readable medium comprising a plurality of machine-readable instructions which, when executed by one or more processors associated with a medical system comprising a manipulator assembly, are adapted to cause the one or more processors to perform a method comprising:
receiving, from a sensor of a user device of the medical system, position or orientation information for one or more landmarks in an environment, and
directing a manual movement of a portion of the manipulator assembly by causing a display device of the user device to present guidance for performing the manual movement within imagery overlaid in the environment based on the received position or orientation information, wherein:
causing the display device to present the imagery comprises causing the display device to present the imagery overlaid with a floor surface in the environment to direct the manual movement of the portion of the manipulator assembly along the floor surface, or
the imagery indicates a path from a current location of the portion of the manipulator assembly toward a recommended location of the portion of the manipulator assembly.

26. The non-transitory machine-readable medium of claim 25, wherein the method further comprises:
creating the imagery based on data comprising information selected from the group consisting of: a target location of a port for an entry by the manipulator assembly, an actual location of the port, procedure information, equipment information, operator information, obstacle information, patient information, and a predefined plan for a medical procedure to be performed by the manipulator assembly.

* * * * *